United States Patent
Agarwal

(10) Patent No.: US 12,326,454 B2
(45) Date of Patent: *Jun. 10, 2025

(54) SYSTEMS AND METHODS FOR IDENTIFYING POSITIVE ALLOSTERIC MODULATORS OF ENZYMES TO ENHANCE ACTIVITY

(71) Applicant: Arium BioLabs LLC, Knoxville, TN (US)

(72) Inventor: Pratul K. Agarwal, Knoxville, TN (US)

(73) Assignee: Arium BioLabs LLC, Edmond, OK (US)

( * ) Notice: Subject to any disclaimer, the term of this patent is extended or adjusted under 35 U.S.C. 154(b) by 1164 days.

This patent is subject to a terminal disclaimer.

(21) Appl. No.: 17/068,311

(22) Filed: Oct. 12, 2020

(65) Prior Publication Data

US 2021/0109105 A1  Apr. 15, 2021

Related U.S. Application Data

(60) Provisional application No. 62/914,213, filed on Oct. 11, 2019.

(51) Int. Cl.
  *G01N 33/68* (2006.01)
  *G16B 15/30* (2019.01)
  *G16B 20/00* (2019.01)
(52) U.S. Cl.
  CPC ......... *G01N 33/6803* (2013.01); *G16B 15/30* (2019.02); *G16B 20/00* (2019.02)
(58) Field of Classification Search
  CPC .............................. G16B 20/00; G16B 15/30
  See application file for complete search history.

(56) References Cited

U.S. PATENT DOCUMENTS 8,417,461 B2   4/2013  Agarwal
9,195,795 B2   11/2015 Agarwal

FOREIGN PATENT DOCUMENTS

WO   WO-2013003358 A2 *  1/2013  ........... C12N 9/6491

OTHER PUBLICATIONS

Chitra Narayanan, Khushboo Bafna, Louise D. Roux, Pratul K. Agarwal, Nicolas Doucet, Applications of NMR and computational methodologies to study protein dynamics, Archives of Biochemistry and Biophysics, vol. 628, 2017, pp. 71-80 (Year: 2017).*

(Continued)

*Primary Examiner* — Karlheinz R. Skowronek
*Assistant Examiner* — Emilie A Neulen
(74) *Attorney, Agent, or Firm* — MERCHANT & GOULD P.C.

(57) ABSTRACT

Methods and systems are provided for identifying positive allosteric modulators of proteins. Small compounds that enhance enzyme activity by binding to an allosteric site are identified, by analysis of biophysical and dynamics data for the target protein. More specifically, the present disclosure is directed to identifying and enhancing the dynamics and energetic behavior of distal surface regions that affect catalytic activity. These allosteric regions are identified and ranked for the impact on enzyme activity, based on the transfer of energy from the surface regions to the active site. Methods are described for computationally screening of chemical compounds to determine a binding energy between each chemical compound and each potential allosteric site. Modifications to the chemical compounds can be made to improve the binding energy, increasing the transfer of energy into the active site, and increasing the number of conformations in the functionally important conformations sub-states. Chemical compounds are selected as top ranking (Continued)

positive allosteric modulators based on ability to modify the conformations of the protein to enhance enzymatic activity.

**20 Claims, 29 Drawing Sheets
(23 of 29 Drawing Sheet(s) Filed in Color)**

(56) References Cited

OTHER PUBLICATIONS

Agarwal, A Biophysical Perspective on enzyme Catalysis, Biochemistry 2019, vol. 58, pp. 438-449.
Agarwal, Role of Protein Dynamics in Reaction Rate Enhancement by Enzymes, Journal of American Chemical Society, vol. 127, pp. 15248-15256 (2005).
Ramanathan, et al. Evolutionarily Conserved Linkage Between Enzyme Fold, Flexibility, and Catalysis, PLOS Biology, vol. 9, Issue 11, pp. 1-18 (Nov. 2011).
Chennubhotla, et al., Signal Propagation in Proteins and Relation to Equilibrium Fluctuations, PLOS Computational Biology, vol. 3, Issue 9, pp. 1716-1727 (Sep. 2007).
McClendon, et al., Quantifying Correlations Between Allosteric Sites in Thermodynamic Ensembles, Journal of Chemical Theory and Computation, vol. 5, No. 9, pp. 2486-2502 (2009).
Ramanathan, et al. Computational Identification of Slow Conformational Fluctuations in Proteins, J. Phys. Chem. B., vol. 113, pp. 16669-16680 (2009).
Yu et al., Heat Flow in Proteins: Computation of Thermal Transport Coefficients, The Journal of Chemical Physics, vol. 122, pp. 54902-1-054902-11 (2005).
Xie et al., Excited-State Lifetimes of Far-Infrared Collective Modes in Proteins, The American Physical Society, Physical Review Letters, vol. 88, pp. 018102-1-018102-4 (Jan. 7, 2002).
Ramanathan et al., Protein Conformational Populations and Functionally Relevant Substates, Accounts of Chemical Research, vol. 47, No. 1, pp. 149-156 (2013).
Ramanathan et al., Discovering Conformational Sub-States Relevant to Protein Function, PLOS One, vol. 6, Issue 1, pp. 1-16 (Jan. 2011).
Boehr et al., The Dynamic Energy Landscape of Dihydrofolate Reductase Catalysis, Science, vol. 313, pp. 1638-1642 (Sep. 15, 2006).
Ichiye et al., Anisotropy and Anharmonicity of Atomic Fluctuations in Proteins: Implications for X-ray Analysis, Biochemistry, vol. 27, No. 9, pp. 3487-3497 (1988).
Kenakin, Allosteric Modulators: The New Generation of Receptor Antagonist, Molecular Interventions, vol. 4, Issue 4, pp. 222-229 (Aug. 2004).
Zhang et al., Targeting Bcr-Abl by Combining Allosteric with ATP-Binding-Site Inhibitors, Nature, vol. 463, pp. 501-507 (Jan. 28, 2010).
Lopez-Garcia et al., Allosteric Regulation of Protein Kinase PKC by the N-Terminal C1 Domain and Small Compounds to the PIF-Pocket, Chemistry & Biology, vol. 18, pp. 1463-1473 (Nov. 23, 2011).
Christopoulos, Allosteric Binding Sites on Cell-Surface Receptors: Novel Targets for Drug Discovery, Nature Reviews Drug Discovery, vol. 1, pp. 198-210 (Mar. 2002).
Kar et al., Allostery and Population Shift in Drug Discovery, Current Opinion in Pharmacology, vol. 10, pp. 715-722 (2010).
Eathiraj et al., Discovery of a Novel Mode of Protein Kinase Inhibition Characterized by the Mechanism of Inhibition of Human Mesenchymal-Epithelial Transition Factor (c-Met) Protein Autophosphorylation by ARQ 197, Journal of Biological Chemistry, vol. 286, No. 23, pp. 20666-20676 (Jun. 10, 2011).
Dettori et al., Regulation of the Interaction Between Protein Kinase C-Related Protein Kinase 2 (PRK2) and Its Upstream Kinase, 3-Phosphoinositide-Dependent Protein Kinase 1 (PDK1), Journal of Biological Chemistry, vol. 284, No. 44, pp. 30318-30327 (Oct. 30, 2009).
Hindie et al., Structure and Allosteric Effects of Low-Molecular-Weight Activators on the Protein Kinase PDK1, Nature Chemical Biology, vol. 5, No. 10, pp. 758-764 (Oct. 2009).

\* cited by examiner

SYSTEMS AND METHODS FOR IDENTIFYING POSITIVE ALLOSTERIC MODULATORS OF ENZYMES TO ENHANCE ACTIVITY

BACKGROUND

Control of protein target activity through binding of small chemical compounds is widely of interest for the discovery of new medicine. The conventional paradigm in medicine discovery through drug design seeks small molecules that bind to the primary function site of target molecules such as active sites of protein and enzyme molecules. In this orthosteric paradigm, small molecules bind to the primary site of function tighter than the naturally occurring substrate (s) or cofactor(s) and inhibits the target function through the mechanism of competitive inhibition.

The paradigm of designing drugs based on competitive inhibition at orthosteric sites face challenges due to the binding of the designed ligand molecule to off-target proteins, causing toxicity and unwanted side-effects. This is due to the fact that the primary site on a target molecule is often conserved across a family or superfamily of protein targets. Therefore, molecules that are designed to mimic the binding of substrates/cofactors to the target protein may also show unwanted binding to other proteins, as the orthosteric sites are conserved across family members. For example, the cofactor nicotinamide adenine dinucleotide ($NAD^+$) and its phosphorylated form ($NADP^+$) participate in a wide variety of redox reactions in the cell. Therefore, the binding sites of $NAD^+/NADP^+$ binding proteins show similar features. Compounds designed as full or partial mimics of $NAD^+/NADP^+$ could bind non-specifically to active sites of a wide variety of enzymes that have strong affinity for $NAD^+/NADP^+$.

In yet another example, adenosine triphosphate (ATP) is a common molecule found in the cell that binds to a wide range of proteins. Particularly, the wide class of protein/enzymes known as kinases is known to show the presence of conserved pockets that bind to ATP. Therefore, designing ATP mimic molecules for a particular kinase shows off-target binding of the mimic molecule to other ATP binding proteins including kinases.

In an alternate approach of drug discovery, protein regions on targets that affect activity but are located far away from the primary sites have been targeted for drug design. Sites which differ from the primary site of protein targets but control the target activity are broadly referred to as allosteric sites. While orthosteric sites are conserved across families and super-families of proteins, allosteric sites are not conserved (and have unique structure and properties) and therefore offer the opportunity of targeting specific proteins. The allosteric sites are of wide interest for design of ligands that can serve as allosteric modulators of target activity. One of the major issues in allosteric modulator design is the identification and characterization of allosteric sites on a target of interest. Currently, available options to investigate possible allosteric sites is either through experimental screening or through computational docking.

In the case of experimental screening, a library of small molecules is used to run pharmacological assays and evaluate whether the target is being modulated in a particular way by a small molecule (ligand). Further assays can also identify whether the small molecule is inhibiting through allosteric effects. Unfortunately, in these assays, there is no information available about the location of binding of the small molecule. Therefore, any kind of medicinal chemistry or drug design is typically not possible at this stage. To be able to perform medicinal chemistry the next step is to perform detailed structural studies such as crystallography in the presence of the identified small molecule. This step is particularly time and cost intensive.

Computational docking studies have been used to identify sites of interest on the protein targets. A number of different methodologies exist for examining the surface of the target molecule to find deep concave pockets that can be used for drug design. Unfortunately, the presence of such pockets does not guarantee that they will have allosteric properties and modulate the target activity in desired fashion. The only way to perform allosteric modulator design is to go through the steps of examining each of these sites for strongly binding hit compounds, followed by medicinal chemistry, and eventually evaluation of the control of the target activity in presence of designed compounds through experimental techniques. Once again, this methodology is extremely time and cost intensive. Therefore, there is a need for fast and inexpensive technologies for the identification and characterization of allosteric sites on targets of interest.

The major hurdle associated with allosteric modulator discovery is the ability to reliably discover true allosteric sites that can control target function. In nature, the allosteric sites exist for designed mechanism of control of the protein target. Methods that allow fast and accurate approaches for discovering the true allosteric sites (instead of finding druggable pockets) and the ability to design small molecules that bind to these sites and modulate the function of the protein target will be critical in discovery of safe and highly effective medicines.

Another major challenge is related to the library of small compounds used for drug discovery. Over many decades, chemical libraries containing compounds that can serve as starting points for discovery of medicine have been developed based on properties that favor binding to the orthosteric sites. It is widely acknowledged that the primary binding sites of protein targets are usually deep hydrophobic pockets having space for functional groups that contain flat rings with hydrophobic properties. Unfortunately, such a paradigm has limited the chemical space that can be used to discover new therapeutic molecules based on allosteric modulation. Approaches that allow increasing the chemical space for discovery of allosteric modulators that can be targeted for drug discovery are also being widely sought.

Technologies that allow systematic and reliable discovery of true allosteric sites, followed by design of drug molecules that bind at these allosteric sites and control the activity of protein target in the desired fashion, are hindered by the lack of fundamental understanding of allosteric effects. Methodologies that ensure high rates of successful discovery of true allosteric sites, instead of just finding binding pockets, need to address the fundamental question of where true allosteric sites are located on proteins and what is the mechanism of control of allosteric control at long distances. Even though the allosteric effects have been the topic of intense investigations, the understanding of why these sites exist on proteins far away from the orthosteric sites remains limited.

The traditional approach used for discovery of medicine is based on finding small molecules that inhibit target molecules. In other words, these small molecules significantly reduce or completely eliminate the enzyme activity of the appropriate target (negative modulation). However, the possibility of increasing the enzyme activity of target (positive modulation) offers new opportunities for application in medicine. For instance, ailments that results from enzymes losing activity for either natural reasons (including mutations) or due to exposure to external agents can be treatment with small molecules that increase the rate of enzyme activity through positive modulation.

SUMMARY

In general terms, this disclosure is directed to methods and systems for discovering allosteric sites of target molecules. This disclosure further provides methods and systems for identifying small molecule targets that modulate enzyme activity by binding an allosteric site.

In particular, the invention is based on the new understanding of protein structure, dynamics and function with the role of surrounding environment in protein activity. The understanding of conformational fluctuations that enable the activity of the protein target allows identification of functionally critical conformational sub-states allowing discovering of true allosteric binding sites and mechanism of allosteric function. Further, identification of network pathways that enable energetic coupling between the solvent and active sites, provide the ability to characterize the allosteric sites. The energy flow in these pathways provide the biophysical coupling between the environment and the active site. This disclosure provides methods for identifying true allosteric sites on a protein target, methodology to rank the different allosteric sites in terms of the activity of the impact on the target activity and provide structural information allowing design of allosteric modulators.

In one aspect, a method of identifying positive allosteric modulators of a target enzyme includes: accessing biophysical and dynamics data for the target enzyme; analyzing, with a computing system, the biophysical and dynamics data to identify one or more potential allosteric sites located on a surface remote from an active site of the target enzyme, the potential allosteric sites comprising a plurality of residues energetically coupled to the active site through an energy transfer network of residues within the target enzyme; quantifying a level of energy flow through the energy transfer network between each of the one or more potential allosteric sites and the active site; scoring each of the potential allosteric sites based on druggability and quantity of energy flow from an allosteric site to the active site; selecting one or more of the potential allosteric sites having the best scores to produce a subset of allosteric sites; computationally screening a plurality of chemical compounds to determine a binding energy between each of the subset of allosteric sites and each of the plurality of chemical compounds; selecting a subset of the plurality of chemical compounds having the highest binding energy; computationally modeling the subset of chemical compounds with different functional groups to produce modified chemical compounds with improved binding energy between the chemical compounds and the allosteric sites; computationally modeling the effect of the chemical compounds binding to each of the plurality of allosteric sites on the enzymatic activity of the target enzyme; quantifying each of a plurality of conformations of the target enzyme while bound to the chemical compounds and while not bound to the chemical compounds, the plurality of conformations including at least one conformational sub-state associated with increased enzymatic activity of the target enzyme; ranking the chemical compounds based on ability to modify the conformation of the target enzyme to enhance enzymatic activity by increasing energy flow from an allosteric site to the active site and increasing conformations in the sub-state associated with enzymatic activity; and outputting a subset of top ranking chemical compounds as allosteric modulators for the target enzyme.

In another aspect, a system for identifying positive allosteric modulators of enzymes includes: a processing device; an enzyme database; and a memory device in communication with the processing device. The memory device comprising instructions that, when executed by the processing device, cause the system to: receive, at a user interface, input selecting an enzyme; access biophysical dynamics data for the enzyme from the enzyme database; analyze the biophysical dynamics data to identify one or more potential allosteric sites located remote from an active site of the enzyme, the potential allosteric sites being energetically coupled to the active site through an energy transfer network within the enzyme; quantify a level of energetic coupling between each of the one or more potential allosteric sites and the active site of the enzyme; score each of the potential allosteric sites based on suitability as a druggable site; select one or more of the potential allosteric sites having the best level of energetic coupling and suitability as a druggable site to produce a subset of allosteric sites; computationally screen a plurality of chemical compounds to determine a binding energy between each of the subset of allosteric sites and each of the plurality of chemical compounds; computationally model the effect of the chemical compounds binding to each of the plurality of allosteric sites; quantify each of a plurality of conformations of the enzyme while bound to the chemical compounds and while not bound to the compounds, the plurality of conformations including at least one conformational sub-state associated with increased enzymatic activity of the target enzyme; and present the quantification results on the user interface.

In yet another aspect, One or more non-transitory computer-readable media having computer-executable instructions embodied thereon that, when executed by one or more computing devices, cause the computing devices to perform the following operations: receive input at a user interface of a computing device, the input selecting a target enzyme; access biophysical and dynamics data for the target enzyme from a data store, the biophysical and dynamics data comprising data obtained by one or more of NMR, X-ray crystallography, Cryo-EM, neutron scattering, and hydrogen-deuterium exchange; analyze the biophysical and dynamics data to identify one or more potential allosteric sites located remote from an active site of the enzyme, the potential allosteric sites being energetically coupled to the active site through an energy transfer network within the target molecule; quantify a level of energetic coupling between each of the one or more potential allosteric sites and the active of the target enzyme; score each of the potential allosteric sites based on suitability as a druggable site and quantity of energetic transfer from an allosteric site to the active site; rank each of the potential allosteric sites based on highest score; select a subset of the potential allosteric sites having the highest rank; computationally screen a plurality of chemical compounds to determine a binding energy between each of the subset of allosteric sites and each of the plurality of chemical compounds; computationally model a derived set of chemical compounds based on strong binding compounds with different functional groups to improve the binding on the allosteric sites; computationally model the effect of the chemical compounds binding to each of the plurality of allosteric sites in the derived set; quantify each of a plurality of conformations of the target enzyme while bound to the chemical compounds and while not bound to the compounds by performing molecular dynamics simulations to model vibrational modes of the enzyme, the plurality of conformations including at least one conformational sub-state associated with increased enzymatic activity of the target enzyme; rank the chemical compounds based on achieving increased energy flow from an allosteric site to the active site and increased conformations in the sub-state associated with enzymatic activity; and present a subset of top ranking chemical compounds comprising potential positive allosteric modulators for the target enzyme on the user interface.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

The present disclosure is directed to methods and systems for identifying allosteric sites on enzymes. More specifically, the present disclosure is directed to identifying and/or designing allosteric modulators of enzymatic activity.

The activity of protein function such as enzyme catalysis involves biochemical and biophysical mechanistic aspects. The biochemical mechanism involves interaction between the substrate molecule and residues in the active site of the enzyme. Enzymes function by lowering the activation energy barrier (when compared to reaction in solvent) for a chemical reaction. The active site environment provides a complementary structural and electronic environment to the transition state of the catalyzed reaction. A number of other factors can be broadly categorized as biochemical aspects of lowering the activation energy barrier for the catalyzed reaction. These factors include electrostatic effects and providing an optimal hydrophobic type environment (with certain hydrophilic contacts), which is far different from the solvent surrounded environment. These biochemical mechanisms are part of the "conventional view" depicted in the left panel of FIG. 1. This is the "lock-and-key" model of a substrate fitting into a rigid enzyme.

However, after all the biochemical factors are included there is still a barrier which needs to be overcome by the enzyme catalyzed reaction, and this corresponds to the measured kinetic rate of the protein activity. Typical energy barriers to be overcome require about another 5 to 10 kcal per mole of energy. Some energy barriers may even include requirements exceeding 10 kcal per mole energy. Specialized biophysical features of enzymes provide the additional kinetic energy required to overcome the lowered energy barrier. The ultimate source of this energy is the temperature driven thermo-dynamical fluctuations in the surrounding solvent and environment. For this energy to be transferred into the active site, requires biophysical mechanism of coupling the distal regions of protein (such as the surface regions) to the active site. Such a coupling cannot be explained or calculated based on the traditional view of rigid enzymes, instead requires a new view of protein function including enzyme catalysis.

Figure 1:
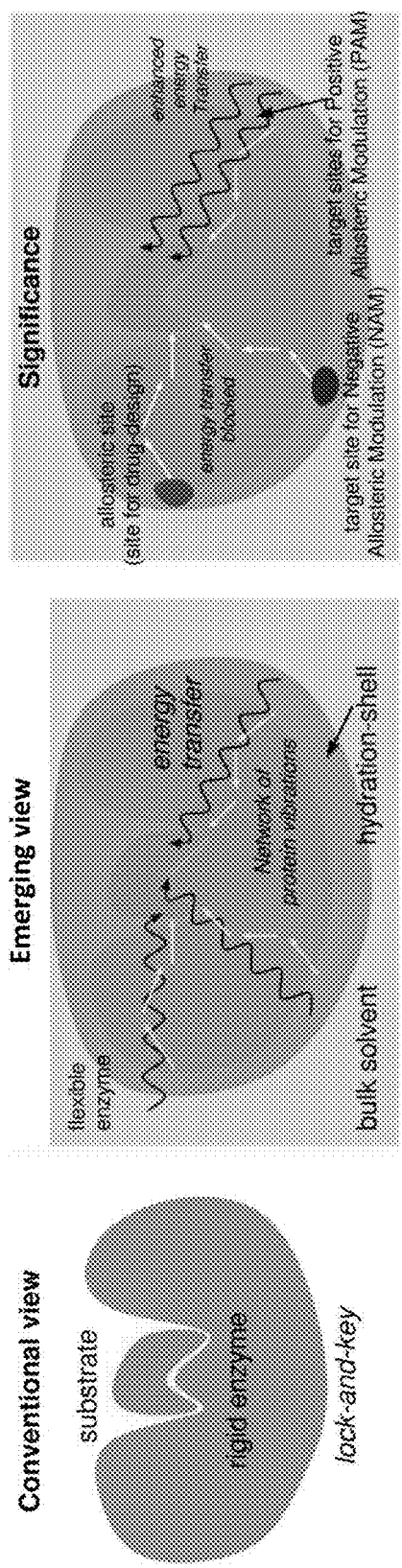
FIG. 1 depicts three schematic representations of an enzyme bound to a substrate, summarizing a current understanding of how enzymes function and their significance for design of allosteric modulators.

The new and emerging view of enzyme function involves a flexible enzyme molecule that is able to collect energy from thermodynamic fluctuations of the bulk solvent and the hydration shell solvent and direct it to the active site. The middle panel of FIG. 1 illustrates the energy transfer from the bulk solvent and hydration-shell to the active site. A large number enzymes contain conserved networks of residues that connect surface regions of the enzyme to the active site. These networks provide thermo-dynamical coupling between the hydration shell, bulk solvent, and the catalyzed reaction. These networks are formed by conserved residues and hydrogen-bonds and hydrophobic interactions between them. On the surface of the enzyme, the function of these networks is to collect thermo-dynamical energy from the solvent. Therefore, these regions are highly flexible floppy loops (showing large dynamical motions) which interact with the solvent. Next to the floppy surface loops are conserved hydrogen bonds and hydrophobic network interactions which span the entire enzyme structure and eventually reach into the active site.

Figure 2:
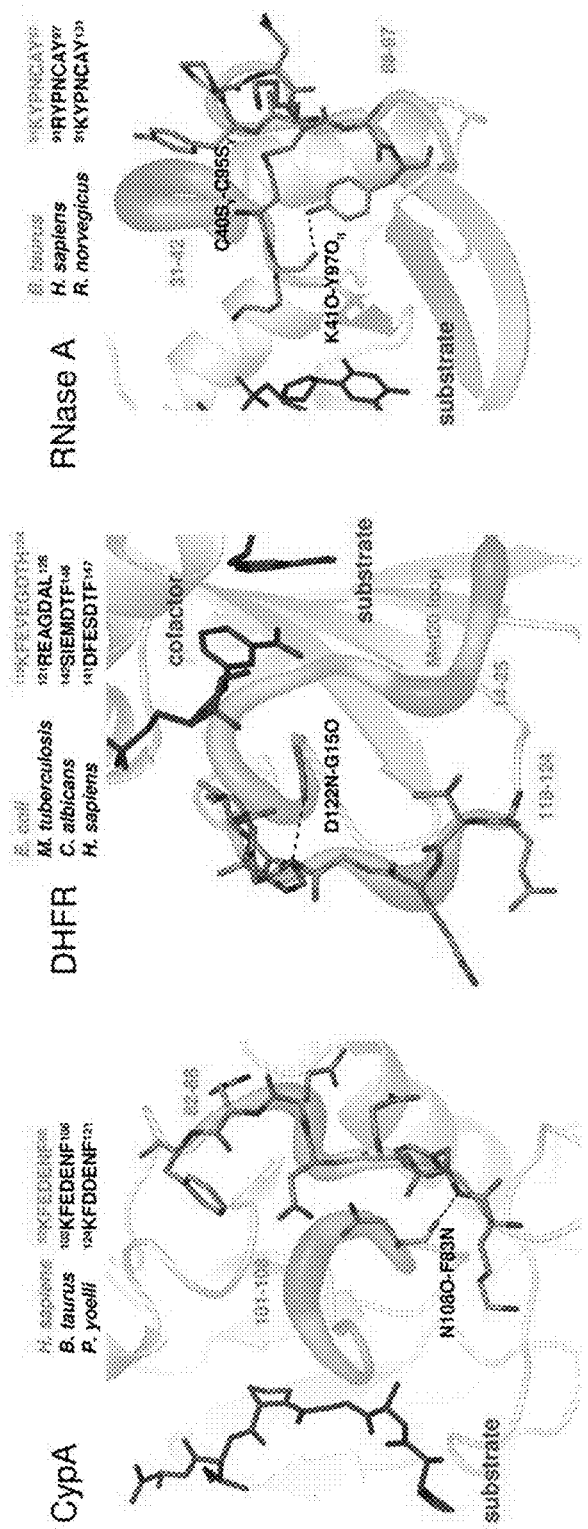
FIG. 2 depicts energy networks present in three different enzyme folds (cyclophilin A, dihydrofolate reductase, and ribonuclease A) and biophysical properties of surface sites, identified through the conserved features of the functionally important surface network regions. These networks are conserved features of the enzyme folds and enable function of enzyme by transferring energy from the solvent to the active site.

These important surface loops have special biophysical properties. Traditional multiple sequence alignment methods do not recognize any specific patterns of conservations at these active (or allosteric) sites. However, a detailed characterization of these surface regions indicates the following features, as depicted in FIG. 2. The surface regions of the energy networks within the enzymes shown (cyclophilin A, dihydrofolate reductase and ribonuclease A) are proposed to be allosteric sites (shown as thick colored tubes), which have the common feature of residues with long side chains. The protein sequence from multiple species is listed on top of each enzyme, indicating very little sequence conservation. The biophysical features preserved for these regions include dynamical flexibility of surface loops, amino acid residues with long side chains, and connectivity of these surface loops to the active sites.

The surface regions are dynamic in nature and enable thermo-dynamical coupling with the solvent. The sequence of these regions does not necessarily contain conserved residues, but instead shows conservation of biophysical property. The biophysical property is optimization of thermo-dynamical coupling with the surrounding solvent. This is accomplished by presence of a large number of residues with long side chains. The side chain on these residues extend out into the solvent, increasing the surface area for the thermo-dynamical coupling. Additionally, these surface regions show energy connectivity to the active site through conserved pathways of residues. The residues in these pathways or networks are connected by hydrogen bonds and hydrophobic interactions to allow the energy transfer from the surrounding solvent into the active site. The number of and positioning of hydrogen bonds from these surface sites to the second layer of protein residues are also important biophysical characteristics of these sites. These surface loops and the 3-D structure in the immediate vicinity of these loops acts as allosteric site.

Figure 3:
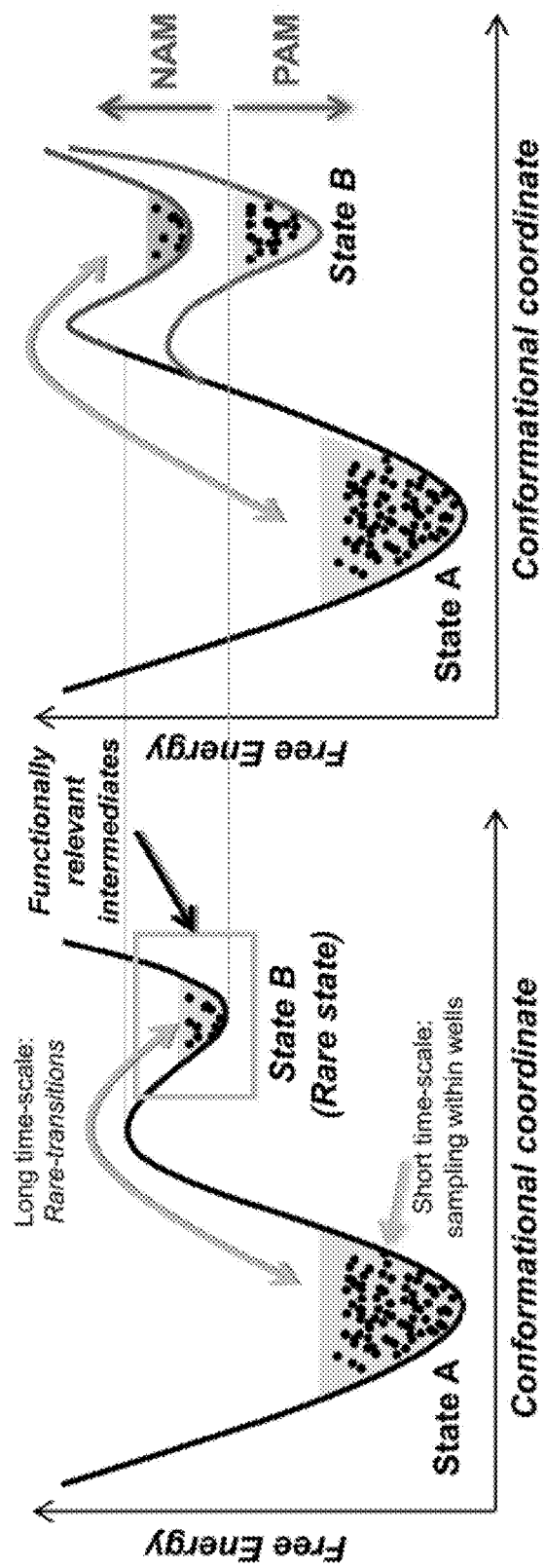
FIG. 3. depicts a schematic showing how an allosteric modulator binding can control the function of a protein target by altering the functionally relevant conformational sub-state populations.

The significance of these networks and the surface regions is illustrated in the right panel of FIG. 1. Once such surface loops of an enzyme are identified that are part of these conserved networks they can be designated as allosteric sites. Then these allosteric sites can be utilized to design small molecules to modulate activity of the enzyme. In particular, binding of a ligand on these sites can change energy flow into the active site and alter the functionally important states and their conformational populations. For example, FIG. 3. depicts how an allosteric modulator binding to a protein target can alter the functionally relevant conformational sub-state populations to affect the target's activity.

A normally functioning protein spends most of its time in a lower energy state (State A), while a sparsely populated state with higher energy (State B) contains functionally relevant intermediate with right structural and electrostatic features to promote the protein function. An allosteric modulator that increases the populations of functionally relevant intermediates or conformational in State B, will improve the activity of the protein, and therefore serve as positive allosteric modulator (PAM). While an allosteric modulator that decreases the number of intermediates in State B will decrease the rate of protein function and therefore serve as negative allosteric modulator (NAM). Thermodynamically, any hindered energy flow will lead to less populations in the State B, and therefore modulators that decrease energy will serve as NAMs.

The following systems and methods describe techniques for identifying allosteric sites on target molecules that affect their activity when bound by small molecules. In particular, the design of small molecules is driven by motivation of interfering (or enhancing) with the dynamics of the surface loops and/or to reduce (or increase) the energetic coupling between the surface and surrounding environment. The decreased energy would in turn decrease the protein activity, while increased energy would in turn increase the protein activity.

Figure 4:
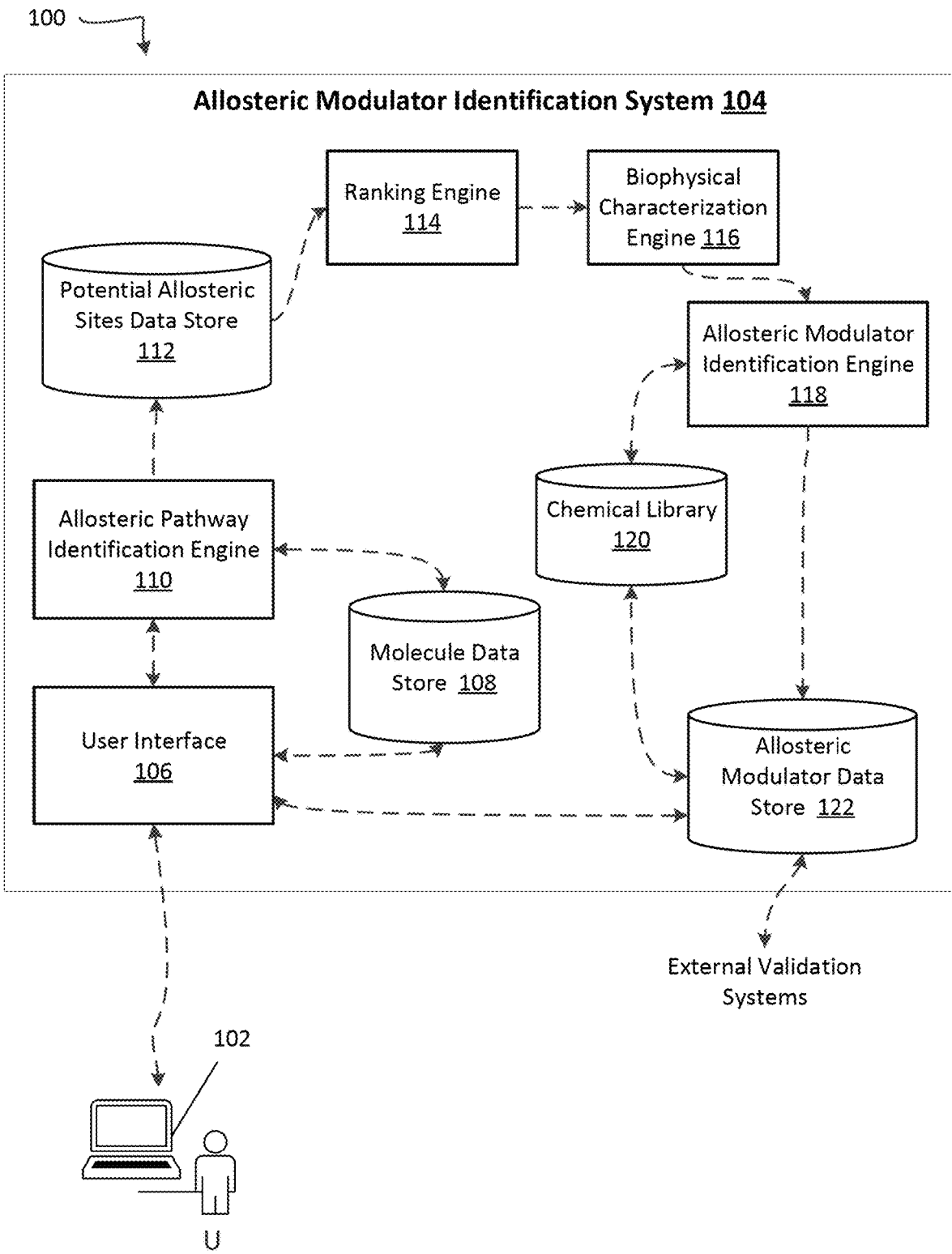
FIG. 4 is a schematic representation of an allosteric modulator identification system.

FIG. 4 illustrates a schematic diagram 100 of an allosteric modulator identification system 104 in communication with a computing device 102. The computing device 102 can communicate with the allosteric modulator identification system 104 through a wired or wireless connection. For example, the computing device 102 could connect to the allosteric modulator identification system 104 through a network such as the Internet, a local area network, or a Bluetooth connection.

The allosteric modulator identification system 104 operates to analyze target molecules to determine locations of potential allosteric sites and to score the potential allosteric sites based on suitability as a druggable site on the molecule of interest. Target molecules can include one or more of a naturally occurring protein, an enzyme, a naturally occurring molecule, or an artificially synthesized molecule. In some embodiments, the target molecule is a protein and the site of designated activity is a protein-ligand or protein-protein binding site.

Druggability is based on compatibility of binding sites with small molecules in terms of volume, topology, and physiochemical properties. Criteria defining suitability as a druggable site can include shape, weight, and charge. Generally, target molecules have a particular activity that is of interest, such as enzyme activity. In some embodiments, the target molecule is an enzyme and the site of designated activity is an active site. In some embodiments, the allosteric modulator identification system 104 includes a user interface 106, a molecule data store 108, an allosteric pathway identification engine 110, a potential allosteric sites data store 112, a ranking engine 114, a biophysical characterization engine 116, an allosteric modulator identification engine 118, a chemical library 120, and an allosteric modulator data store 122.

The user interface 106 operates to present a display of information in textual and graphical form on the computing device 102. The user interface 106 receives inputs from the user U in the form of selections, text input, and data uploads. In some embodiments, the input is received through an input device in communication with the computing device 102 such as a mouse, keyboard, microphone, or touchscreen. The visual display presents options to the user through the computing device 102. In some embodiments, the options include menus to select molecules or enzymes of interest. The user interface 106 also operates to present data to the user U in the form of text, images, tables, charts, graphs, and 3-D models. Inputs received at the user interface 106 can be used to manipulate the data and the displays of the data.

The molecule data store 108 operates to store information about molecules that can be accessed by the user interface 106 and allosteric pathway identification engine 110. In some embodiments, the molecules perform particular designated activities that are of interest. The molecules could be a naturally occurring protein, an enzyme, a naturally occurring molecule, or an artificially synthesized molecule. The molecule data store 108 includes names of molecules, structural information about the molecules, and optionally may also include data on biological activity of interest. In some embodiments, if structural data is not available for the target of interest then structural information from similar members, such as members of same superfamily, is included. In some embodiments, the molecule data store 108 is an enzyme database.

In some other embodiments, the molecule data store 108 stores biophysical and dynamics data that is obtained by computational analysis of internal movements of the molecule that affect its designated activity. In some embodiments, this computational analysis is performed using quasi-anharmonic analysis (QAA). In some embodiments, this computational analysis is performed using root-mean-square-fluctuations (RMSF) analysis, principal component analysis (PCA), or normal mode analysis (NMA), or time-averaged normal coordinate analysis (TANCA). In some embodiments, the biophysical dynamics data is obtained by one or more of nuclear magnetic resonance (NMR), X-ray crystallography, cryogenic electron microscopy (Cryo-EM), neutron scattering, and hydrogen-deuterium exchange.

The allosteric pathway identification engine 110 operates to analyze biophysical dynamics data for a selected target molecule to identify potential allosteric sites on the molecule that are remote from the site of designated activity. Computer simulations such as molecular dynamics (MD) simulations and information collected from experimental techniques are used to analyze different enzyme-substrate complex conformations. Regions of high flexibility on the surface of the enzyme are identified as well as a network of residues connecting these regions to the active site of the enzyme. In some examples, quasi-anharmonic analysis (QAA) is employed to analyze the enzyme conformations.

The potential allosteric sites data store 112 operates to store information about the potential allosteric sites that were identified by the allosteric pathway identification engine 110. This information can be stored in tables and organized based on identifiers of enzymes or locations of allosteric sites. The information could include lists of residues connecting an allosteric site to an active site; descriptive information about an enzyme such as a molecular weight and function; and 3-D structural information.

The ranking engine 114 operates to evaluate and rank the potential allosteric sites. Information regarding potential allosteric sites for a particular molecule are accessed from the potential allosteric sites data store 112 by the ranking engine 114. The ranking engine 114 quantifies a level of energetic coupling between each potential allosteric site and the site of designated activity for the target molecule. In some embodiments, the conductance of energy flow along various atom-atom contacts is calculated using data from molecular dynamics simulations. The ranking engine 114 then scores each potential allosteric site based on its suitability as a druggable site. The ranking engine 114 then ranks the potential allosteric sites based on their score.

The biophysical characterization engine 116 operates to characterize protein target structure and sequence alignment allowing for identification of the networks within the protein.

The allosteric modulator identification engine 118 operates to computationally evaluate chemical compounds for suitability as modulators of allosteric sites. The effect of binding of the chemical compounds to each of the potential allosteric sites are computationally modeled. In some embodiments, the conformational landscape of the can be analyzed using experimental approaches such as NMR, X-ray crystallography or similar techniques for molecular structural determination. In some embodiments, QAA is performed to computationally simulate difference sub-states when the modulator is present and absent.

The chemical library 120 stores information about a multitude of small molecules. In some embodiments, the chemical library 120 is accessed by the allosteric modulator identification engine 118 and the allosteric modulator data store 122. In some embodiments, the chemical library 120 is accessed from a remote server that is maintained by a third party. For example, the chemical library could be a database designed for virtual screening of molecules such as the ZINC (zinc15.docking.org) database of commercially available chemical compounds.

The allosteric modulator data store 122 operates to store information about small molecules that have been identified as allosteric modulators by the allosteric modulator identification engine 118. In some embodiments, the allosteric modulator data store 122 can be accessed by the user interface 106 to display information about the molecules. In some embodiments, other external computing systems used to validate the allosteric modulators can access the information in the allosteric modulator data store 122.

Figure 5:
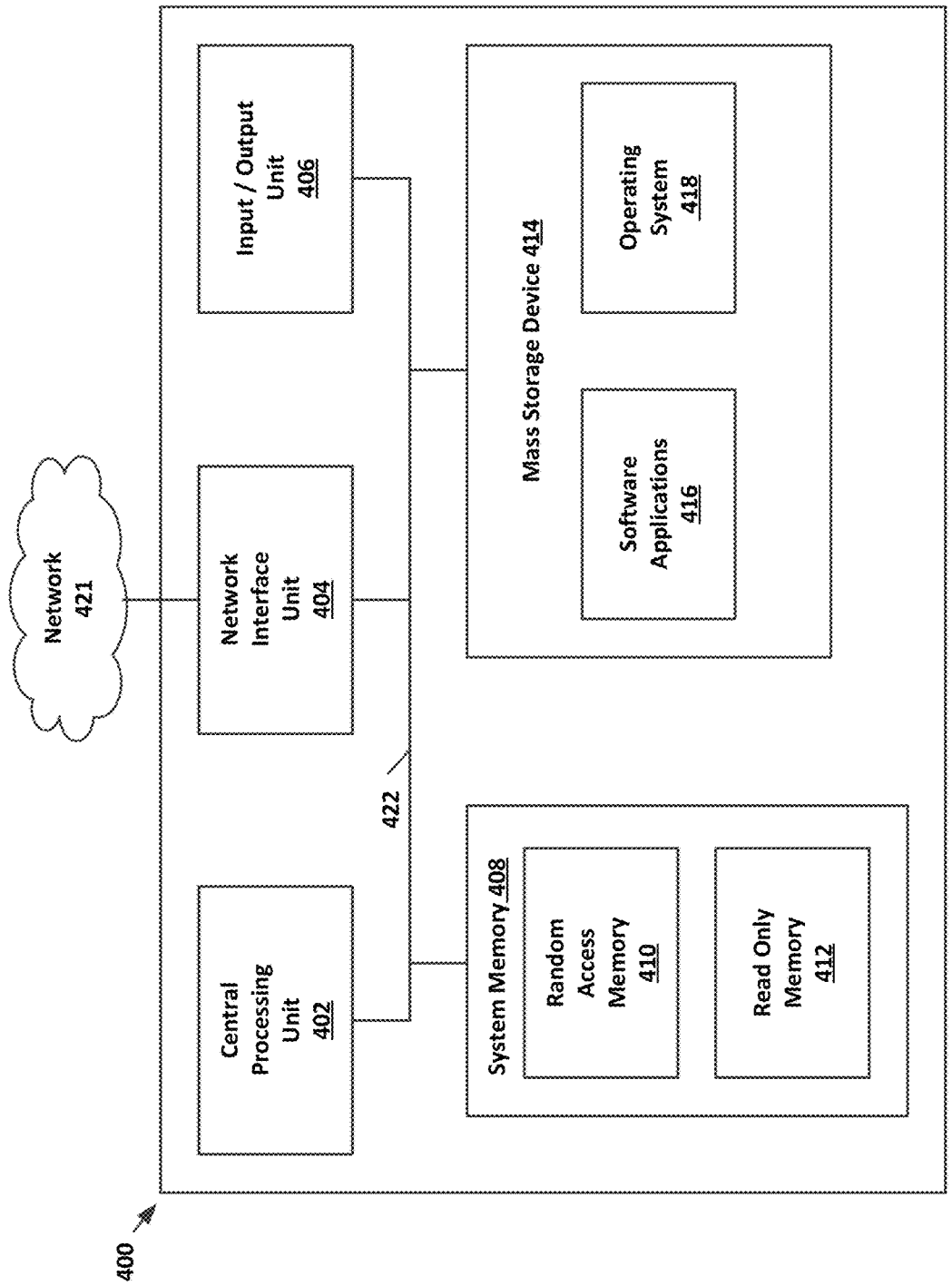
FIG. 5 is a schematic representation of an example computing device usable to implement various aspects of the system of FIG. 4.

FIG. 5 is a block diagram illustrating an example of the physical components of a computing device 400. The computing device 400 could be any computing device utilized in conjunction with the allosteric modulator identification system 104 such as the computing device 102 of FIG. 4.

In the example shown in FIG. 5, the computing device 400 includes at least one central processing unit ("CPU") 402, a system memory 408, and a system bus 422 that couples the system memory 408 to the CPU 402. The system memory 408 includes a random-access memory ("RAM") 410 and a read-only memory ("ROM") 412. A basic input/output system that contains the basic routines that help to transfer information between elements within the computing device 400, such as during startup, is stored in the ROM 412. The computing system 400 further includes a mass storage device 414. The mass storage device 414 is able to store software instructions and data such as instructions to implement the allosteric pathway identification engine 110 or allosteric modulator identification engine 118.

The mass storage device 414 is connected to the CPU 402 through a mass storage controller (not shown) connected to the system bus 422. The mass storage device 414 and its associated computer-readable storage media provide non-volatile, non-transitory data storage for the computing device 400. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU 402 can read data and/or instructions. In certain embodiments, the computer-readable storage media comprises entirely non-transitory media.

Computer-readable storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device 400.

According to various embodiments, the computing device 400 can operate in a networked environment using logical connections to remote network devices through a network 421, such as a wireless network, the Internet, or another type of network. The computing device 400 may connect to the network 421 through a network interface unit 404 connected to the system bus 422. It should be appreciated that the network interface unit 404 may also be utilized to connect to other types of networks and remote computing systems. The computing device 400 also includes an input/output controller 406 for receiving and processing input from a number of other devices, including a touch user interface display screen, or another type of input device. Similarly, the input/output controller 406 may provide output to a touch user interface display screen or other type of output device.

As mentioned briefly above, the mass storage device 414 and the RAM 410 of the computing device 400 can store software instructions and data. The software instructions include an operating system 418 suitable for controlling the operation of the computing device 400. The mass storage device 414 and/or the RAM 410 also store software instructions, that when executed by the CPU 402, cause the computing device 400 to provide the functionality discussed in this document. For example, the mass storage device 414 and/or the RAM 410 can store software instructions that, when executed by the CPU 402, cause the computing system 400 to implement the method 500 described in FIG. 6.

Figure 6:
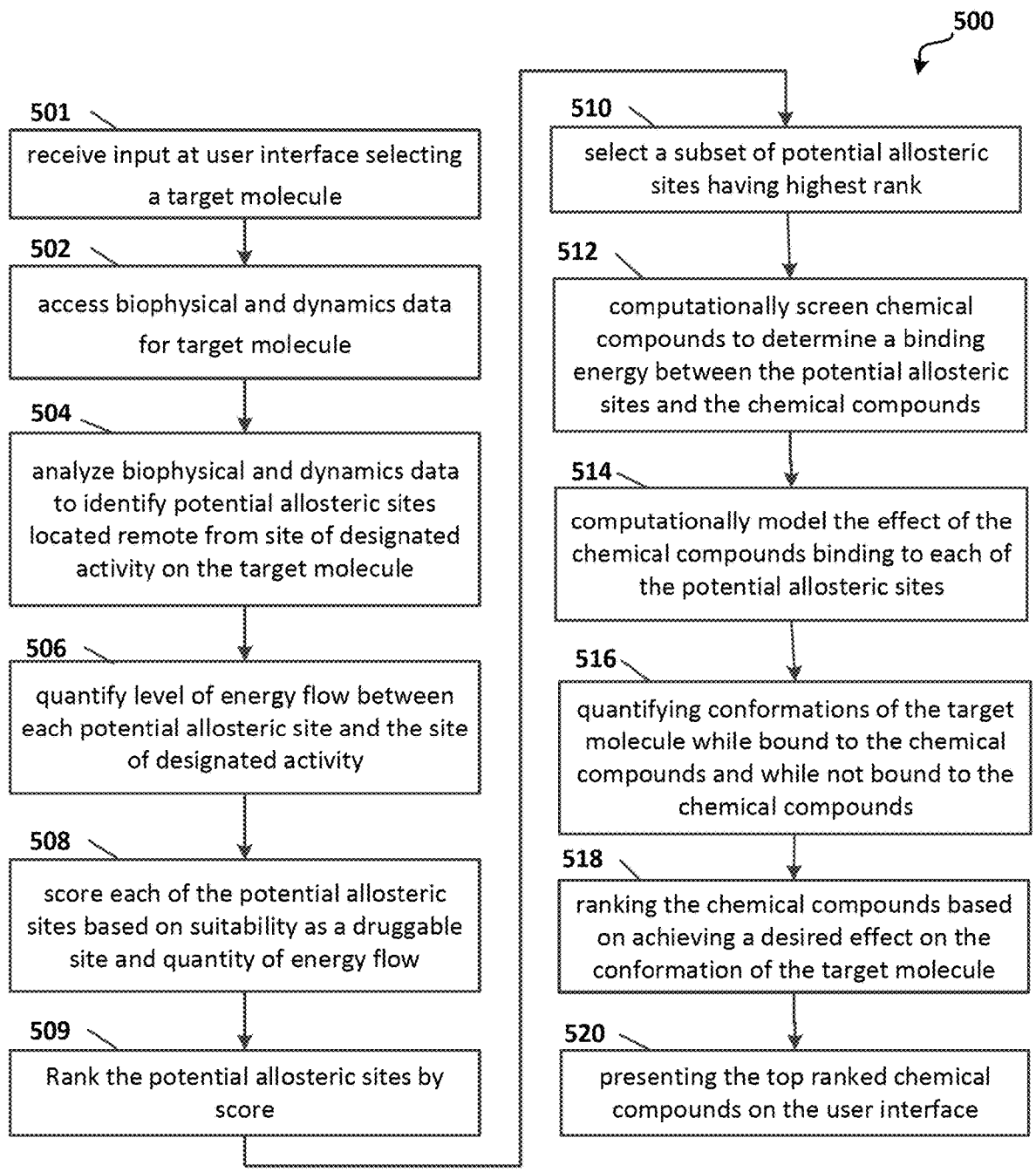
FIG. 6 is a flow diagram illustrating an example method of identifying allosteric modulators of a target molecule.

FIG. 6 is a flow chart of an example method 500 of identifying allosteric modulators of a target molecule. In some embodiments, the target molecule is an enzyme. This method could be performed by the allosteric modulator identification system 104 of FIG. 4. Other computing systems could be utilized to perform the operations of the method 500. In some embodiments, one or more operations are performed without the aid of a computing device.

At operation 501, input is received at a user interface selecting a target molecule. The user interface could be the user interface 106 displayed on the computing device 102 operated by the user U. The input could be received by means such as a stylus, a keyboard, a touchscreen, voice input, or a mouse. The target molecule could be selected from a list or input manually with text or chemical structure input. The target molecule has a designated activity of interest. For example, the target molecule could be an enzyme protein that catalyzes a particular reaction.

At operation 502, biophysical and dynamics data for the target molecule is accessed. In some embodiments, the biophysical and dynamics data was previously generated and stored in the molecule data store. In some embodiments, biophysical and dynamics data can be accessed directly from the source of the data, such as computer simulations, experimental techniques or published literature.

At operation 504, the biophysical and dynamics data is analyzed to identify potential allosteric sites located remote from a site of designated activity on the target molecule. The potential allosteric sites are energetically coupled to the site of designated activity through an energy transfer network within the target molecule. Various techniques can be used to analyze protein dynamics including root-mean-square-fluctuations (RMSF) analysis, normal mode analysis (NMA), time-averaged normal coordinate analysis (TANCA), quasi-harmonic analysis (QHA), Gaussian network model (GNM), and quasi-anharmonic analysis (QAA). Different sub-states of the molecule's conformations are evaluated to identify regions of high flexibility on the molecule. In some examples, this could be a loop of residues on the surface of an enzyme protein. In some embodiments, the potential allosteric sites that are identified are stored in a data store 112 until they are accessed and analyzed by other computing modules.

At operation 506, a level of energetic coupling between each potential allosteric site and the site of designated activity is quantified. In some examples, the site of designated activity is an active site on an enzyme. In some embodiments, the energetic coupling can be quantified by determining the conductance of energy flow along various atom-atom contacts. This can be calculated using molecular dynamics simulations to model vibrational modes of the molecule. Small amounts of kinetic energy are added at different areas of the protein surface and energy flow from those areas to the active site are monitored.

At operation 508, each of the potential allosteric sites are scored based on suitability as a druggable site as well as the site's energy conductance. Networks with residues having high energy conductance are scored higher because energy is transferred from allosteric site to active site more efficiently. Additionally, the allosteric sites are evaluated for their suitability as a druggable site by examining the site for the presence of cavities or pockets in which a small molecule could bind, or identifying patterns in the protein residues for commonalities with known druggable proteins.

At operation 509, the potential allosteric sites are ranked by their score. In some embodiments, this function can be performed by the ranking engine 114 of FIG. 4.

At operation 510, a subset of the potential allosteric sites having the highest rank are selected. The allosteric sites with the best level of energetic coupling and suitability as a druggable site are selected for further study.

At operation 512, chemical compounds are computationally screened to determine a binding score between each of the subset of potential allosteric sites and the chemical compounds. The chemical compounds could be accessed from a chemical library 120 and screened using the allosteric modulator identification engine 118.

In some embodiments, a derived set of chemical compounds is computationally modeled based on strong binding compounds with different functional groups to improve the binding on the allosteric sites. Particular emphasis is on locking the dynamical motions of the flexible regions of the allosteric site. Compounds that rearrange/disrupt hydrogen bonds between the surface protein residues and the next layer of the network, to disrupt/decrease the energy flow, is also an aspect of the design.

At operation 514, the effect of the chemical compounds binding to each of the potential allosteric sites is computationally modeled. This function can also be performed by the allosteric modulator identification engine 118.

At operation 516, conformations of the target molecule are quantitatively characterized both when the molecule is bound to the chemical compounds and when not bound to the chemical compounds. In some embodiments, the quantification results are presented on the user interface. In some embodiments, the protein conformations associated with the protein activity are determined using one or more of root-mean-square-fluctuations (RMSF) analysis, principal component analysis (PCA), normal mode analysis (NMA), time-averaged normal coordinate analysis (TANCA), quasi-harmonic analysis (QHA), and quasi-anharmonic analysis (QAA).

At operation 518, the chemical compounds are ranked based on their effect on the conformation of the target molecule. In some instances, the top compounds will have an inhibitory effect on the molecule's designated activity. In other instances, the top compounds will have an activating effect on the molecule's designated activity.

At operation 520, the top ranked chemical compounds are presented on the user interface. In some embodiments, the chemical compounds can also be saved to a data store or communicated to other computing systems.

The top ranked chemical compounds are potential allosteric modulators that can be validated using various experimental techniques to determine efficacy of the modulators. Such in vitro techniques can include spectrophotometric assays, radiometric assays, mass spectrometry, multiple injection method studies, isothermal titration calorimetry studies, stopped-flow kinetics, steady state kinetics, and pre-steady state kinetics measurements.

The invented methodology described in this disclosure enables the identification of the protein dynamics, and conformational sub-states associated with protein activity such as enzyme catalysis. When combined with sampling of protein activity of interest, this can be used to identify functionally important sub-states associated with the activity. The information obtained further allows identification of surface regions (far away from the active site) and the network of residues that connect these regions to a site of activity thereby enabling thermo-dynamical coupling of surrounding solvent with the activity of the protein. These surface sites are designated as potential allosteric sites, as wide variety of evidence from previous investigations indicate that such sites modulate the protein activity. Using this information, it is possible to discover the mechanism of allosteric modulator already known to bind to such sites. Further this information is used to virtually screen compounds that bind and modulate the activity of the protein target. Changes to the hit compounds for improving the modulation of target activity is performed computationally and then can be verified using experimental approaches.

Design of Positive Allosteric Modulators

In certain applications, it is desirable to increase the target activity of enzymes. In one embodiment, the described methodology can be used to design positive allosteric modulators (PAMs) which increase the activity of the enzyme.

For example, the presence of the PS48 in the PIF pocket of PDK1 is known to improve the activity of the enzyme 1.4-4.4 folds over the base activity. Therefore, PS48 acts as a PAM for PDK1.

The biophysical basis of PAM design, in our approach, is based on improving the thermo-dynamical energy coupling between the enzyme surface and solvent and/or enhancing the energy flow from these surface sites of the enzyme to the activity center. The series of steps is similar to the design of negative allosteric modulators, consisting of modeling the protein activity, discovering the allosteric sites based on discovery of the conformational sub-states and the dynamical network residues. This is followed by screening of compounds that score well for interactions on these sites. However, for discovery of the PAMs, the fundamental difference is to discover compounds that show the presence of increased number of conformations in the conformational sub-states and also show increased energy flow into the active site. It can be envisioned that in certain cases the allosteric site that do not rank highly for energy flow could be more suitable for the design of positive allosteric modulator. Therefore, different target allosteric sites need to be investigated for design of PAMs.

An example of the application of PAMs is in search of therapies for exposure to nerve gas agents (NGAs). Organophosphate compounds have been used as NGAs in biological attacks and weapons, which act by covalently modifying the enzyme acetylcholinesterase (AChE). One approach for design of therapy and treatment for NGAs exposure is to design PAMs for the enzyme AChE. In cases where a large fraction of the AChE enzyme molecules has been modified by NGAs and rendered incapable of conducting their natural enzymatic activity, a medicinal molecule that increases the activity of the remaining functional AChE molecules would enable the overall activity to be similar to the pre-exposure levels. This is depicted schematically in FIG. 27, where an example indicates that if exposure to NGA such as sarin, causes $\frac{3}{4}^{th}$ of the AChE enzyme molecules to be damaged and results a loss in 75% of the enzyme activity; a PAM which increases 4 fold activity of remaining $\frac{1}{4}^{th}$ of the AChE molecules would result in an overall substrate turnover similar to the pre-exposure level. In other examples, much higher fold improvements would allow more severe exposure levels to be treated.

EXAMPLES

Computational methods for characterization of Protein Dynamics and Conformational Sub-States Protein dynamics or vibrational modes of a protein (representing protein dynamics) are modeled by a set of displacement vectors for each atom in the protein. Several methods are available to compute the vibrational modes of a molecular system such as a protein. A list of suitable techniques for use with the methods and systems described in this disclosure to compute the protein vibrational modes are discussed below.

Normal Mode Analysis (NMA)

This method computes vibrational modes of a molecular system by diagonalization of the Hessian matrix. Assuming the molecular system has N atoms, the Hessian matrix is a 3N×3N matrix. The elements of the matrix are the second order energy derivatives with respect to the displacement of atomic positions in the x, y, z directions. The elements can be computed analytically or computationally. Once the Hessian matrix is computed, it is diagonalized to solve for the eigenvectors and eigenvalues.

$$\varepsilon_i F = \varepsilon_i \omega_i \qquad \text{(Eq. 1)}$$

The time-scale of molecular vibration is determined by taking the inverse square root of the eigenvalues (ε) obtained after diagonalization. The eigenvector (ω) corresponding to the eigenvalue represents the vibrational modes, which are a set of displacement vectors for the atoms in the molecular or the protein conformation.

Time-Averaged Normal Coordinate Analysis (TANCA):

This method is similar to NMA in the sense that the protein vibrational modes are obtained by diagonalization of the Hessian matrix. However, NMA suffers from some limitation when considering a highly flexible molecular system such as a protein. NMA uses a reference structure and the eigenvalues and eigenvectors thus obtained are only relevant to the reference starting structure. The method therefore weights highly toward the high frequency motions and less toward the low frequency motions. Moreover, the low frequency obtained using NMA are not reliable for molecular conformations that differ considerably from the reference structure for NMA. (For protein functions, the low frequency motions are more important as they are associated with the high energy barriers between different conformational sub-states.)

Techniques such as TANCA can partially overcome this problem by diagonalization of the Hessian matrix which has been constructed numerically by averaging the elements over time. This allows the fast frequency motions to be removed by averaging and provides more accurate low frequency modes that are relevant for protein function.

Quasi-Harmonic Analysis (QHA)

This method computes protein vibrational modes from a set of protein conformations that are sampled using either the molecular dynamics (or Monte-Carlo) type simulations. QHA is a powerful method in obtaining vibrational modes that are representative of longer time-scales or the low frequency vibrational, by utilizing the information from a set of structures which may be separated by a long-time scale—or from different parts of the protein conformational space. The vibrational modes are obtained by diagonalization of the atomic fluctuation matrix. For a protein with N atoms, the atomic fluctuation matrix, F is a symmetric 3N×3N matrix with term $F_{\alpha\beta}$ defined as:

$$F_{\alpha\beta} = \langle m_\alpha^{1/2}(x_\alpha - \langle x_\alpha \rangle) m_\beta^{1/2}(x_\beta - \langle x_\beta \rangle) \rangle \qquad \text{(Eq. 2)}$$

where α, β run through the 3N degrees of freedom in Cartesian space and $m_\alpha$ is the mass of atom corresponding to the αth degree of freedom and $x_\alpha$ are the Cartesian coordinates of the atom corresponding to the αth degree of freedom. Quantities in ⟨⟩ denote an average determined from molecular dynamics simulation. To obtain the eigenmodes (vibrational modes) diagonalization of the atomic fluctuation matrix is performed (see Eq. 2). The time-scale of protein vibration is determined by taking the inverse square root of the eigenvalues (ε) obtained after diagonalization. The eigenvector (ω) corresponding to the eigenvalue represents the protein vibrational modes, which are a set of displacement vectors for the atoms in the protein confirmation. Note one of the benefits of QHA is that multiple MD trajectories can be combined to construct the atomic fluctuation matrix—thus allowing vibrational modes to be computed that represent conformational changes between different areas of the protein conformational space.

Gaussian Network Model (GNM):

This type of calculation uses coarse-grained normal mode analysis to obtain protein vibrational modes. These calculations use a simple parameter harmonic potential for the particles in the system. The eigenmodes are obtained by the diagonalization of Kirchhoff's matrix, which is similar to Hessian matrix, but uses a reduced model of the protein and treats the protein motions as Gaussian type motions.

Irrespective of the type of method described above, for a protein with N atoms, there are 3N-6 protein vibrational modes. These modes describe a variety of motions within the protein. The modes with fast time-scales indicate repeated movements of atoms, or a small group of atoms that occur as many as a billion to trillion times per second. The intermediate time scales are associated with concerted movements of a group of protein residues. The intermediate time-scales span several orders of magnitude and are associated with motions of loop regions, alpha helices and beta-sheets. The modes associated with the slowest time-scales are associated with the overall conformational fluctuations of a protein that involve major domain(s) or even the entire protein. The protein motions at different time-scales correspond to kinetic energy to allow overcoming of a variety of energy barriers encountered by the protein in the functional landscape. The fastest motions in the range of $10^{-15}$ seconds to $10^{-12}$ seconds, overcome small energy barriers. The intermediate motions in the range of $10^{-12}$ seconds to $10^{-6}$ seconds are important for overcoming medium height barriers. The slowest motions at scale of $10^{-6}$ seconds and slower (i.e. $>10^{-6}$ seconds) are important for overcoming large energy barriers. Therefore, using vibrational modes associated with the slowest motions can find conformations within the conformational energy landscape that are separated by high energy barriers. Likewise, the vibrational modes associated with the intermediate and faster motions are useful for inducing more local conformational changes, like the movement of a loop region, an alpha helix, or the side chains of individual residues. Accurate estimates of energy associated with the protein vibrational modes is currently not available, however, the lower estimations would correspond to energy associated with vibrations of individual bonds (<1 kcal/mol) and on the higher end correspond to movement of entire protein domains (5-10 kcal/mol or higher).

Quasi-Anharmonic Analysis (QAA)

This relatively new methodology allows automated discovery of a hierarchy of sub-states associated with the conformational ensemble of proteins. Utilizing atomistic level MD simulations of proteins or protein in association with other molecules (such as binding partners or enzyme-substrate complex) as input, this methodology pays close attention to the anharmonic nature of internal protein motions and pursues the higher-order statistics of the internal motions. One of the most important advantages of this approach is that it allows clean separation between the conformational sub-states, by projecting the conformations sampled during the molecular dynamics simulations in a lower dimensional space represented by QAA vectors. Characterization of the populations in these sub-states for any relevant properties (such as internal energy, distance order parameter, or reaction coordinate) allows the detailed characterization. In addition, to identifying these sub-states, the motions associated within the sub-states and inter-conversion between the sub-states provide new insights into the inter-relationship between protein structure, motions and function.

Figure 7:
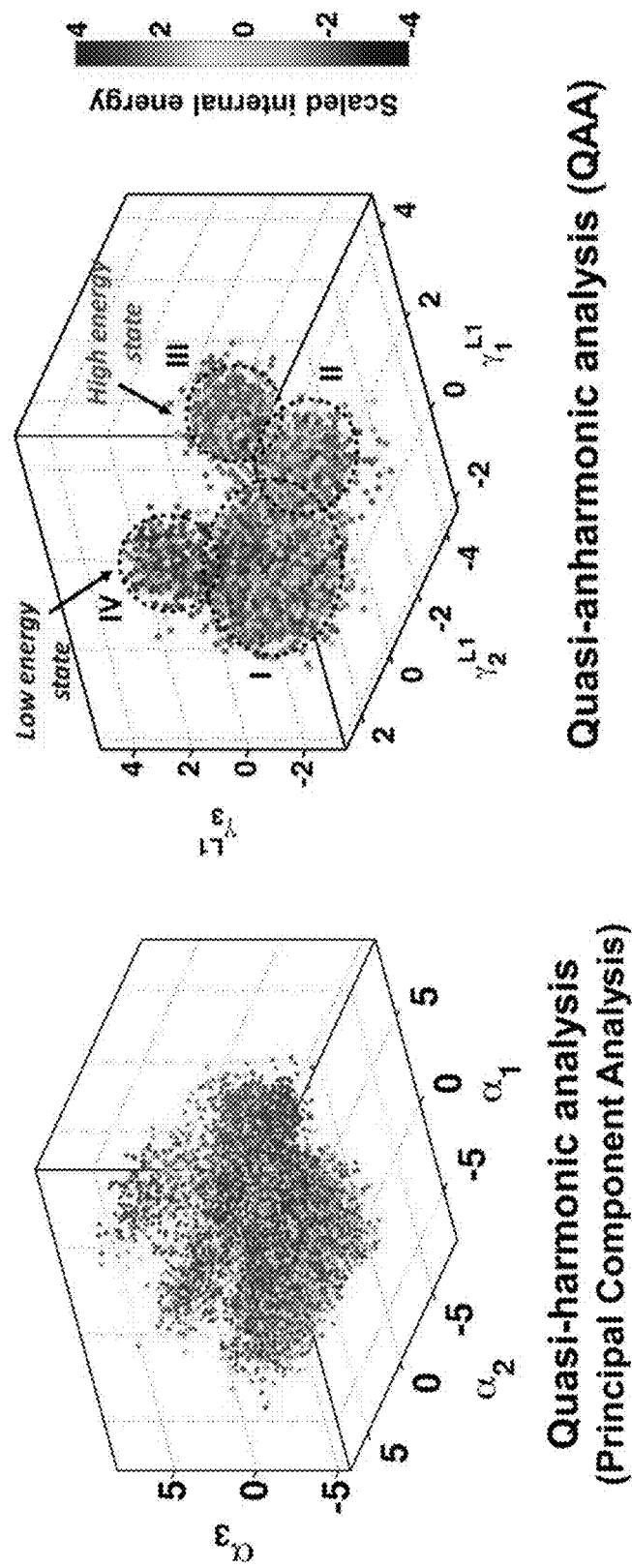
FIG. 7 depicts the unique benefit of using the approach quasi-anharmonic analysis (QAA) versus other approaches such as principal component analysis or quasi-harmonic analysis (QHA). QAA provides clear identification of homogeneous conformational sub-states. The results shown are from protein human ubiquitin and the coloring is based on scaled conformational (internal) energy. The conformations were obtained from molecular dynamics simulations.

QAA allows characterization of conformational sub-states along a reaction pathway. A hierarchical description of the sub-states along the reaction pathway identifies sub-states with structural and dynamical features critical for attainment of the transition state. One of unique benefits of QAA is that it allows identifying conformational states with homogenous properties correctly, which is not possible by second order methods such as principal component analysis and QAA. For example, as depicted in FIG. 7, the energy values are homogeneous in sub-states identified by QAA (right panel) but not by QHA (left panel).

Example 1

Discovering Networks, Conformational Sub-States and Surface Sites Associated with Protein Activity and Identification of Allosteric Sites The enzyme human CypA catalyzes the cis/trans isomerization of peptidyl-prolyl amide bonds in peptides and proteins substrates. NMR spin relaxation studies have provided important insights into the movement of the protein residues in presence and absence of the substrate which coincides with the catalytic cycle. The NMR data indicated that the intrinsic dynamics of the protein in this enzyme coincides with the time-scale (about 9000/second) of the substrate turnover step (the rate limiting step) and promotes the reaction mechanism.

Computational studies identified a hierarchy of motions coupled to the reaction. Analysis of fast motions, slow conformational fluctuations and cross-correlation of the motions over the course of isomerization reaction led to the discovery of a network of protein vibrations in CypA coupled to its reaction mechanism (FIG. 2). This network extends from surface loop residues of the enzyme all the way to the active-site, through a series of hydrogen bonds and hydrophobic interactions. The protein motions in this network occur on the time-scales ranging from picosecond to microsecond-millisecond (time scale of the reaction). Genomic and structural analyses indicated that the residues and hydrogen-bonds forming crucial points in the network are conserved in several cyclophilin structures of species ranging from bacteria to human. NMR relaxation studies have observed motions in the network residues coupled to the substrate turnover step.

The biophysical impact of discovered network on the CypA reaction mechanism was revealed by monitoring changes in the active-site environment that are introduced by the conformational fluctuations of the network residues. Computational analysis of these changes showed that the progress of reaction is correlated with the fluctuations in the substrate-enzyme interactions, which in turn are controlled by the motions and conformational fluctuations in the CypA network.

The relative orientations and the motions of these network residues have shown to be conserved aspect of isomerase fold. These observations are consistent with the reaction mechanism from previous X-ray crystallographic studies that indicate that the interaction between target proline residue of the substrate and active-site hydrophilic and hydrophobic residues of enzyme play a crucial role during the reaction. An interesting observation is that the maximum enzyme stabilization of the substrate occurs close to transition-state (consistent with the transition-state stabilization theory).

The role of these conformational fluctuations could, therefore, be also interpreted as concerted internal protein movements, which facilitate in stabilization of the transition-state. Hence, these are conformational fluctuations are termed as reaction promoting as they: (1) bring together the enzyme active-site in an organized state such that the all the structural elements are correctly positioned and (2) allow more reaction trajectories to become productive.

A number of other enzymes have also shown the presence of networks and the role of internal motions on enzyme catalysis including dihydrofolate reductase (DHFR), ribonuclease A, liver alcohol dehydrogenase, lipase B and others. In some enzyme systems, the thermodynamical motions or fast motions have been shown to aid in enzyme catalysis. However, CypA and DHFR specifically show the presence of motions and conformational fluctuations that are intrinsic motions associated with the topology of the enzyme. Therefore, these motions are not random in nature but are a designed part of the enzyme structure as they have been observed to be present even in apo enzyme and enzyme complexes, and the rate of these repeated motions can be measured reproducibly using different techniques.

It should be noted that distal regions in all proteins can be connected through a serious of interactions, however, experimental data (with controls) is required to before a series of interactions can be considered as a network impacting enzyme catalysis. In particular the effect of elimination or substitution of the network interactions (through mutations) on enzyme activity should be clearly demonstrated. For non-enzyme systems the existence of such networks is difficult to characterize and validate. The conversion of substrate(s) to product(s) by enzyme systems offer development of ways to monitor change in protein function associated with changes introduced in protein structure by techniques such as mutations. PDZ domain is an example of non-enzyme systems where the existence of such networks has been demonstrated using statistical coupling approach and tested with the use of mutational studies.

QAA was successfully used to organize the complex conformational landscape of the peptidyl-prolyl cis/trans isomerization (PPIase) activity catalyzed by human enzyme cyclophilin A (CypA), into a multi-scale hierarchy of conformational sub-states. The conformational landscape associated with the PPIase activity was sampled using molecular dynamics in combination with umbrella sampling with the isomerized amide bond as reaction coordinate. Over 100,000 conformations collected from the MD simulations were analyzed using QAA.

Figure 8:
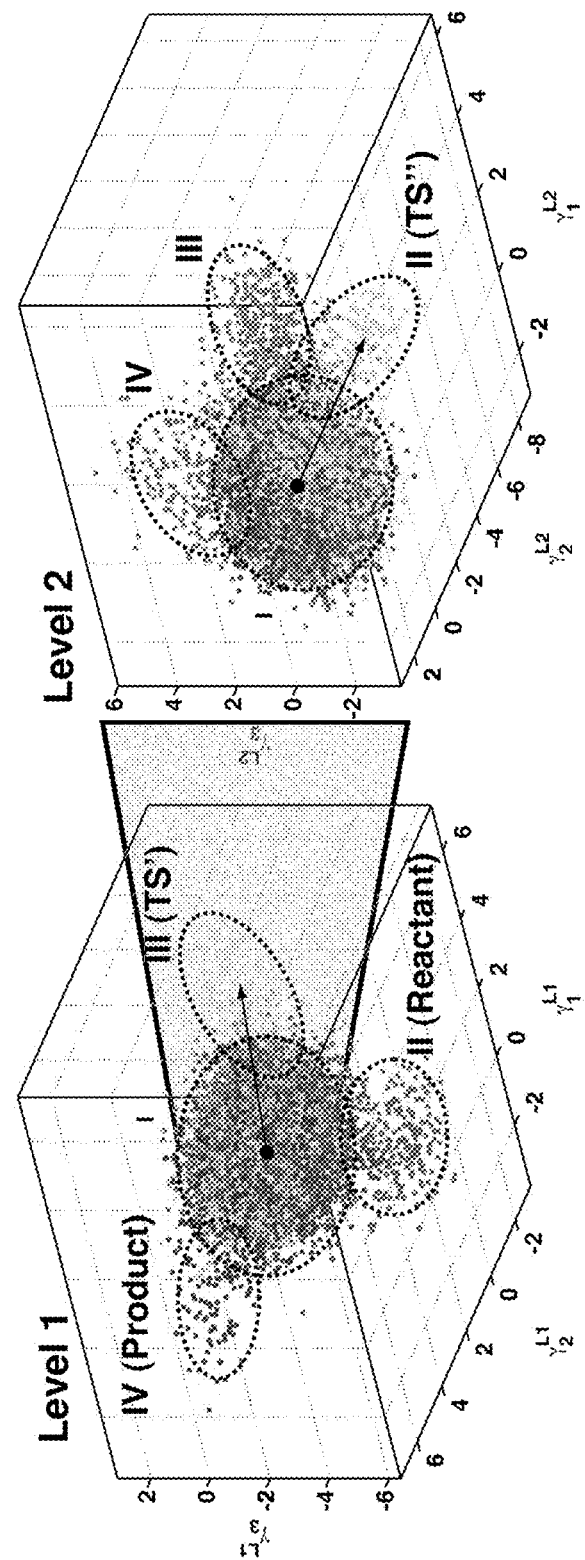
FIG. 8 depicts the use of quasi-anharmonic analysis (QAA) to identify the conformational landscape of cyclophilin A, characterized for peptidyl-prolyl cis-trans isomerization activity. On the left, first round of QAA shows decomposition of the landscape into Reactant (R), Product (P) and Transition State (TS') sub-states. The right panel shows level 2 decomposition performed by taking the mixed conformation sub-state and repeating QAA only on this sub-state.

FIG. 8 shows the results of QAA analysis. On the left, the first round of QAA shows decomposition of the landscape into Reactant (R), Product (P) and Transition State (TS') sub-states. The TS' here is close to but does not correspond to the transition state (TS), which is defined as the highest point on the free energy profile (see FIG. 8). Further analysis of the remaining (mixed) conformations were required to identify the values closer to the true transition state (TS"). Further analysis for Level 2 decomposition is performed by taking the mixed conformation sub-state and repeating QAA only on this sub-state.

Figure 9:
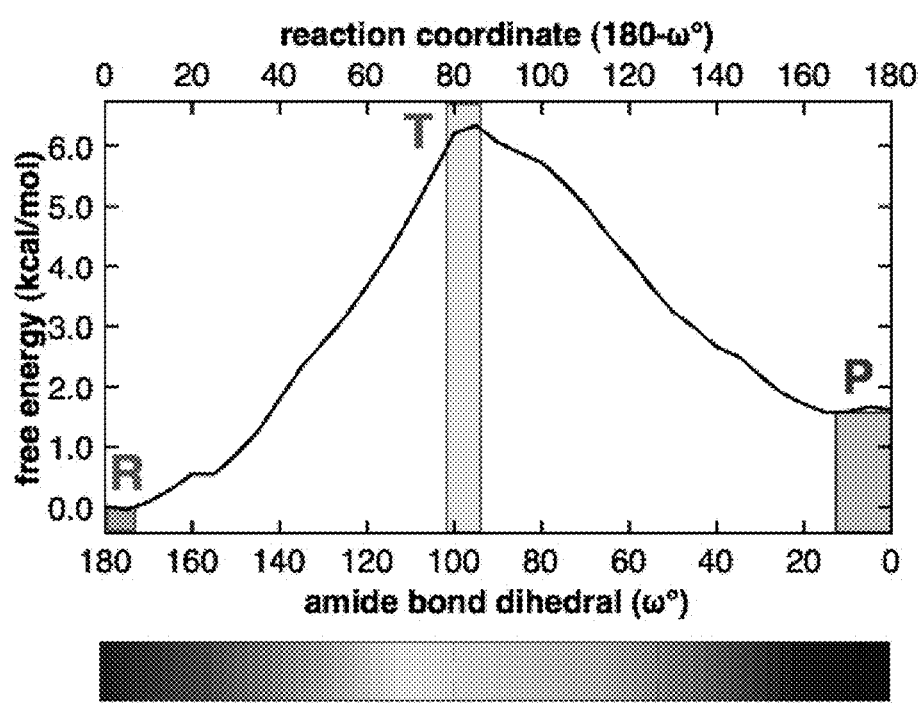
FIG. 9 depicts the free energy profile associated with the peptidyl-prolyl cis-trans isomerization activity of the human cyclophilin A protein. The reaction coordinate is color coded as the reaction proceeds from Reactant (R) state to Product (P) state. The highest point of the free energy profile is defined as the transition state (T or TS).

FIG. 9 depicts the free energy profile associated with the peptidyl-prolyl cis-trans isomerization activity of the human cyclophilin A protein. The amide bond is rotated as the reaction proceeds. The reaction coordinate in this analysis was defined as a value equal to 180—the value of amide bond dihedral angle. The reaction coordinate is color coded as the reaction proceeds from Reactant (R) state to Product (P) state. The highest point of the free energy profile is defined as the transition state (T or TS).

Figure 10:
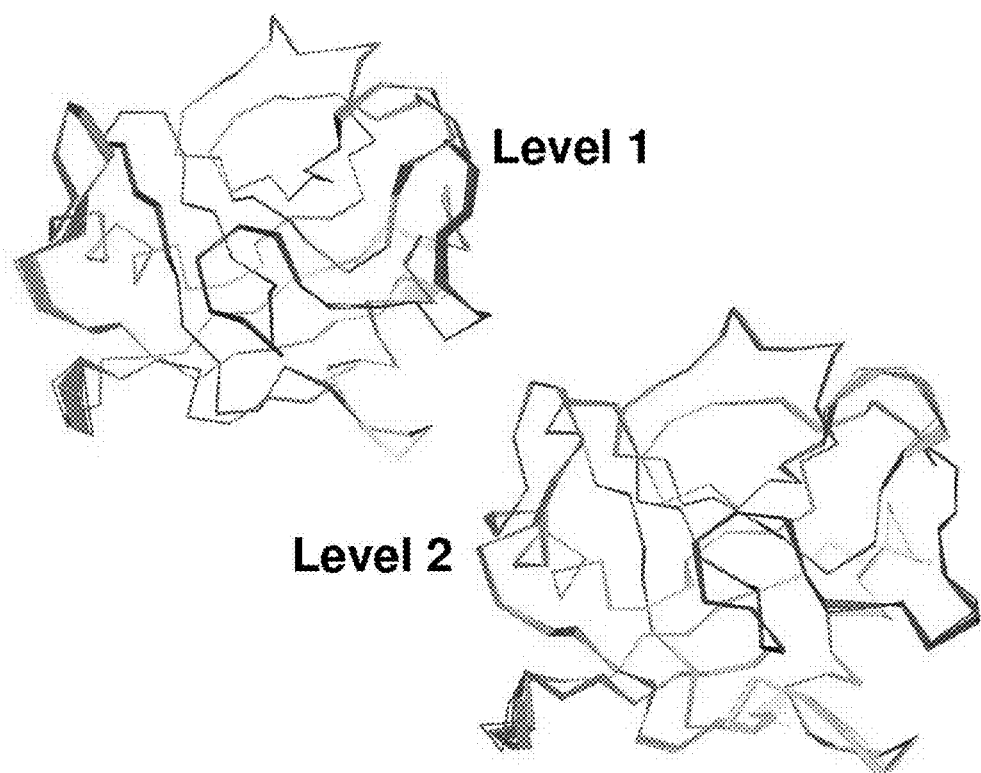
FIG. 10 depicts identification of the conformational changes associated with the protein (human cyclophilin A) as the protein transitions from the ground state into the functionally relevant TS' (Level 1) or TS" sub-state (Level 2).

FIG. 10 depicts identification of the conformational changes associated with the protein (human cyclophilin A) as the protein transitions from the ground state into the functionally relevant TS' or TS" sub-state. The conformational change is depicted in a movie like fashion with only the protein backbone shown. The regions colored are the regions showing largest changes in the conformations. These conformational changes correspond to the black arrows in FIG. 7, as the protein transitions from the central sub-states into the TS' (for Level 1) and TS" (for Level 2) respectively.

QAA allowed identification of independent component analysis (ICA) vectors or modes. The projection of enzyme-substrate complex conformations on the first three dominant QAA modes allows identification of clusters or sub-states (labeled I, II, III and IV in FIG. 8). These sub-states can be characterized for the region of reaction pathway they correspond to by inspecting the reaction coordinate (FIG. 9): reactant, product or near the TS (TS'/TS"). For mixed populations without clear separations into sub-states, the QAA analysis can be repeated in a multi-level fashion (FIG. 8). For CypA, two levels provide qualitative insights as sub-states near TS (the green/yellow colored sub-states TS' and TS") were identified. Protein fluctuations within the sub-states or between the sub-states can be obtained by comparing the changes in protein conformations. For example, the dark black arrows in the figure (both at level 1 and 2) indicate conformational fluctuations associated with enzyme-substrate complex visiting the sub-states TS' and TS" (FIG. 8).

Figure 11:
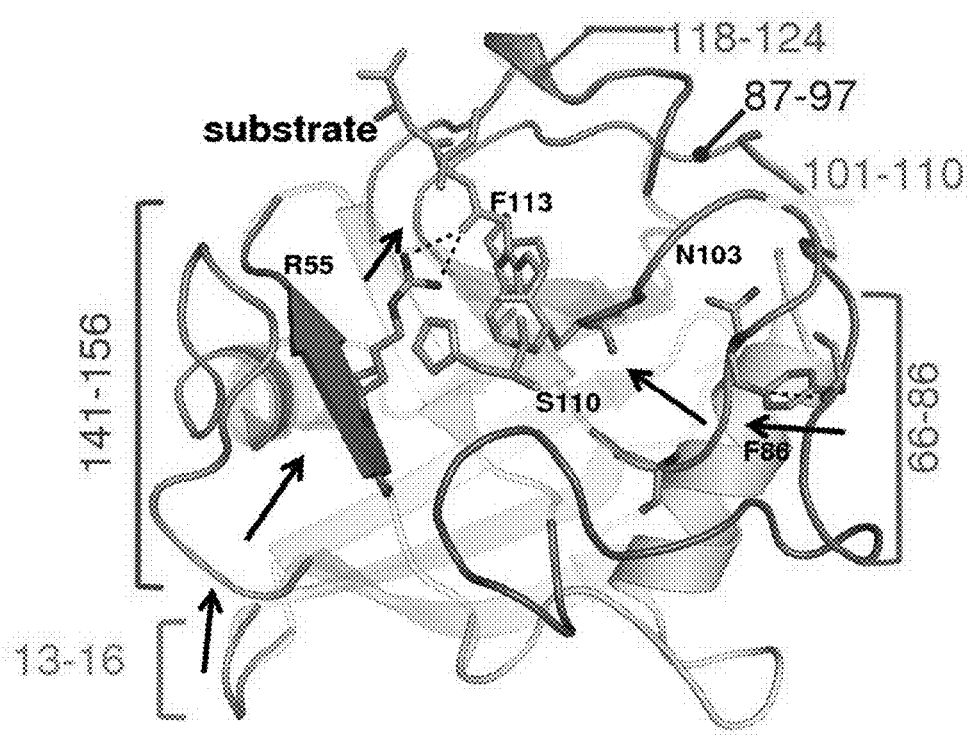
FIG. 11 depicts identified surface loops and pathways in human cyclophilin A connecting these surface loops to active site.

FIG. 11 depicts identified surface loops and pathways in human cyclophilin A connecting these surface loops to active site. These conformational changes associated with the protein as is transitions into the functionally relevant sub-state associated with the peptidyl-prolyl cis-trans isomerization activity (shown in FIG. 8 and FIG. 10) allowing the identification of these surface regions and the network pathways which connect them into the active site. Any changes on these surface loops will have impact on the protein activity, therefore, these surface regions would serve as allosteric sites for this protein's activity.

FIG. 7 depicts the unique benefit of using the approach quasi-anharmonic analysis versus other approaches such as principal component analysis or quasi-harmonic analysis. The same conformational landscape when subjected to the analysis based on these different method gives different results. The QAA approach identifies the correct conformational sub-states of high and low energy while the other approaches do not provide clear separation into homogenous sub-states. The results shown are from protein human ubiquitin and the coloring is based on scaled conformational (internal) energy. The conformations were obtained from molecular dynamics simulations.

For CypA, the enzyme fluctuations that allow visiting the TS' and TS" correspond to the motions of previously identified network promoting catalysis (FIG. 11). Detailed characterization of the motions that lead to the sub-state (TS'/TS") identified regions of high flexibility on the surface and the network of residues connecting these regions to the active site (FIG. 11). The list of network residues is similar to the results obtained from different techniques including NMR spectroscopy and other computational results.

Overall, these results indicate that QAA allows the identification of the conformational sub-states associated with enzyme activity of a protein. Detailed analysis of the functionally relevant conformational sub-states allows the identification of rate limiting conformational transitions that allow access into these sub-states. Further structural analysis of these sub-states and conformational transitions allows the identification of surface regions of the enzyme with large dynamical motions on the surface, and the network of residues that connect these surface regions to the active site.

Ranking of Allosteric Sites and Networks based on Energy Flow

Once discovered, the allosteric sites can be assigned a score for their ability to control the target activity. Based on the assigned score, the ranking of these allosteric sites could serve as an important metric in drug discovery efforts. An allosteric site with high druggability score but little or no impact on protein activity would lead to loss of time and effort. Therefore, it is important to assign a score or ranking of each discovered allosteric site for their impact on protein activity. In other efforts, already discovered "binding pockets" from other computational docking approaches can also be assigned an energy transfer or coupling score as a metric for its ability to control target activity.

In one approach, to obtain the efficiency of energy flow within proteins, an information theoretic approach can be used in combination with molecular dynamics simulations. In this approach the ability of protein residues (or atoms) to participate in energy flow is investigated by observing its ability to receive and pass a "signal" to its neighbors. The localized neighbors can include solvent (if the atom is exposed to the solvent), ions, and other protein atoms. Using the frequency of the number of times a residue makes contact with another residue (either via hydrogen bonding or van der Waals contact) the expected time for a "signal" to propagate from one residue (for example located on the surface of the protein) to another residue (for example located in the active site) can be computed. In information theory, this expected time of signal propagation within a network is investigated using hit times, which can also be used to estimate how a protein may communicate with its neighbors.

Figure 12:
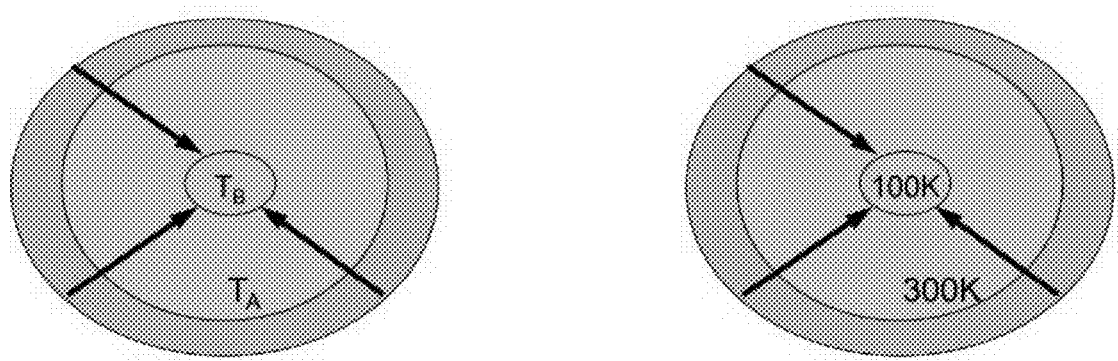
FIG. 12 is a schematic diagram illustrating energy flow within a protein as a result of a temperature gradient.

In another approach to calculating the efficiency of energy transfer, conductance of energy flow along various atom-atom contacts is calculated using data from molecular dynamics simulations. Molecular dynamics simulations provide atomic coordinates and velocities associated with each atom as the systems evolves. Conductance of energy is calculated using the coordinates and velocity information. In regular molecular dynamics system, a constant system temperature is maintained throughout the system. However, to investigate the preferential pathways of energy flow through the protein, a gradient of energy is created between two different parts of the system as depicted in FIG. 12. For example, to investigate the energy flow between the protein surface and active site, the simulations can be performed at temperature $T_A$ while the active site is kept at a lower temperature $T_B$. The lowering of temperature is performed by reassigning the atomic velocities at a predefined number of steps. This results in creating an energy gradient and inducing a result energy flow into the active site. In the right panel of FIG. 12, the sample temperature values used were $T_A$=300K and $T_B$=100 K.

Any two atoms in contact will have a slightly different temperature due to the temperature gradient. Two atoms are deemed to be in contact if their distance in the native conformation, $r_{ij}^{NAT}$, satisfies the condition $$r_{ij}^{NAT} < \sigma_i + \sigma_j + \frac{1}{2}(\delta r_i + \delta r_j) \quad \text{(Eq. 3)},$$

where $\sigma_i$ is the van der Waals radius of atom i and $\delta r_i$ is the standard deviation for the distribution of displacements of atom i from the average conformation. The heat flux flowing from atom i to atom j can then be estimated with an expression analog to Fourier's law, $$J_{i \to j} = w_{ij} k_B (T_i - T_j) \quad \text{(Eq. 4)}.$$

$T_i$ is the temperature of atom i, determined from its time-average kinetic energy via $$3/2 k_B T_i = \frac{1}{2} m_i \langle v_i^2 \rangle \quad \text{(Eq. 5)}.$$

The heat transmission frequency $w_{ij}$ between atoms i and j is derived from the corresponding element of the covariance matrix of the mass-weighted atomic displacements from the average conformation, $$w_{ij}^2 = \left| \frac{k_B (T_i + T_j)}{\langle m_i^{1/2} \delta \vec{r}_i \cdot m_j^{1/2} \delta \vec{r}_j \rangle} \right|. \quad \text{(Eq. 6)}$$

Once interatomic fluxes are computed, fluxes between any two residues R and R' can be obtained by adding up interatomic fluxes between pairs of atoms, $$J_{R' \to R} = \sum_{i \in R'} \sum_{j \in R} J_{i \to j}. \quad \text{(Eq. 7)}$$

The energy conductance (also called energy connectivity) of residue R is defined as the sum of all heat fluxes entering and exiting the residue, $$C_R = \sum_{R'} |J_{R' \to R}|. \quad \text{(Eq. 8)}$$

Residues with a high energy conductance are thus important in channeling the energy flowing from the solvent towards the reaction center where the energy-sink atoms are located. The obtained information of energy conductance can be used in two ways for allosteric site scoring and ranking. First, the values of $C_R$ associated with each network residue can be tabulated. The network pathway score is simplest form an average of $C_R$ values of the network residues; therefore, a network consisting of residues with high $C_R$ values will show higher score of energy transfer efficiency. In another embodiment a multiplicative score is used to assign the network ($C_R$ values of all network residues are multiplied). In yet another embodiment, if no information about the allosteric sites is available then residues showing high $C_R$ values are connected and inspected further for the existence of the network and allosteric sites.

Example 2

Energy Efficiency Scoring

NADP$^+$ binding proteins play important roles in cellular redox reactions. A number of these proteins have been investigated widely for presence of protein residue networks associated with their activity. These include investigations of the enzyme dihydrofolate reductase (DHFR) from *Escherichia coli* (EcDHFR), *Mycobacterium tuberculosis* (MtDHFR), *Candida albicans* (CaDHFR) and humans (hDHFR). Conserved networks have been identified in each of these enzymes. These enzymes catalyze the transfer of hydride between the NADP$^+$ cofactor and a substrate.

To investigate the energy flow and conductance along the networks, a combination of MD simulations were performed in an informatics approach. In the MD simulations, small amounts of excess kinetic energy were added in different areas of the protein surface and then the energy flow from these areas into the active site was monitored. As depicted in FIG. 12, this was done to keep the active site at a temperature of 100 K while the remaining enzyme and solvent was kept at a temperature of 300 K.

Molecular dynamics simulations were carried out near equilibrium in a quasi-steady state. Every 1 picosecond (ps), velocities from a subset of atoms in the immediacy of the hydride transfer reaction site were rescaled such that the total kinetic energy was decreased by 9.552 kcal/mol. These atoms are termed the energy-sink atoms. The selected amount of energy extracted is such that would result in an immediate cooling of the energy-sink atoms to a final temperature of 100 K, provided the atoms were at an initial temperature of 300 K. This energy decrease is high enough to provide a signal above thermal noise. The extracted energy was immediately transferred to the solvent by rescaling solvent atom velocities. An amount of energy equal to 9.552 kcal/mol divided by the total number of water molecules was added to every water molecule. As a result of repeating this energy redistribution every 1 ps, a heat flux converging towards the protein and approximately constant for time scales>>1 ps arises. A net flow of heat enters the protein through the surface residues and makes its way to the energy sink atoms, and then back to the solvent ending the cycle. Simulations were carried out for a total of 200 ps.

In addition to the heat flux, a temperature gradient within the protein is formed such that the energy-sink atoms have an average temperature of about 100 K, while the protein atoms far from the energy-sink atoms and in contact with the solvent have an average temperature of about 300 K.

Figure 13:
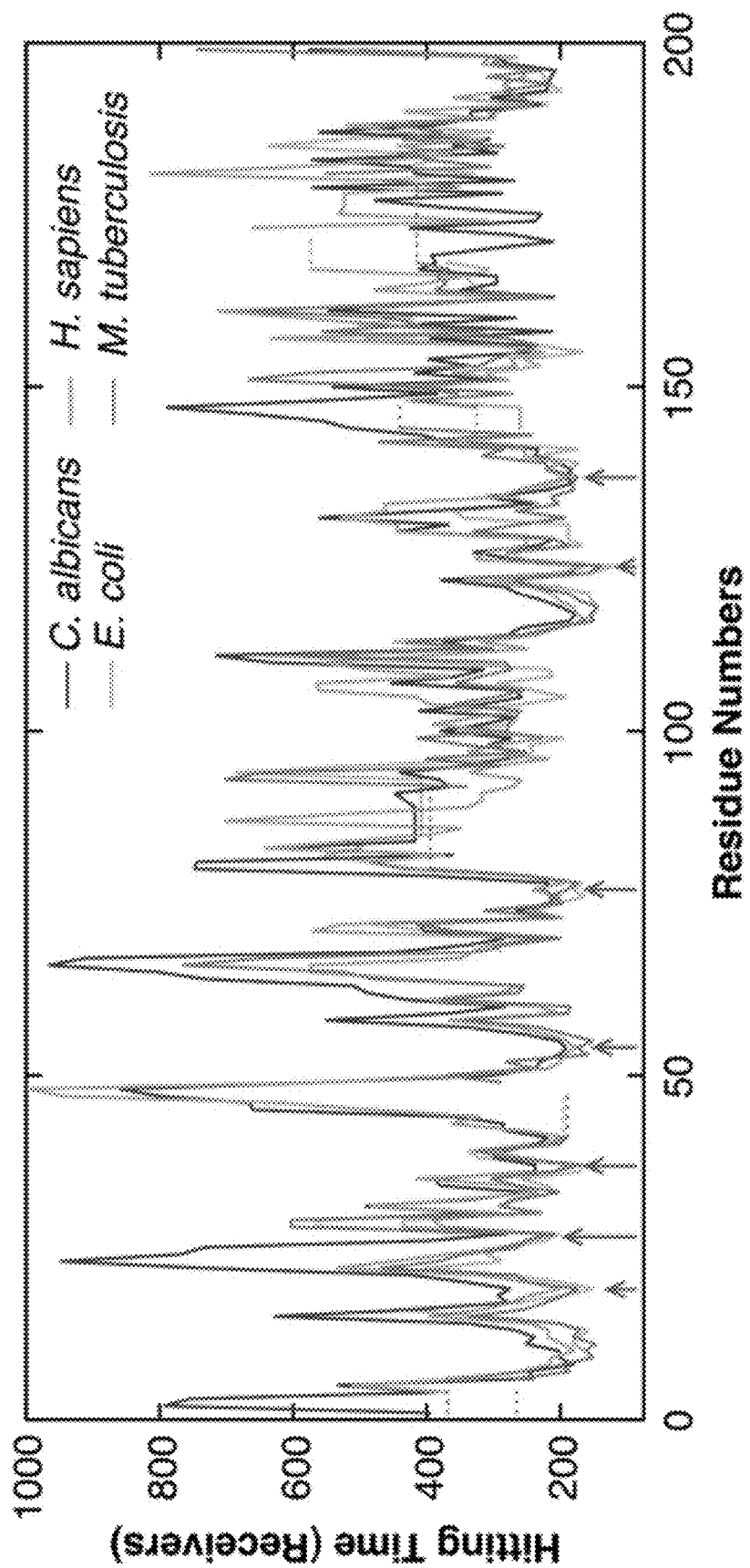
FIG. 13 is a line chart showing hit time plotted against residue numbers for dihydrofolate reductases (DHFRs) from the four different species: *Escherichia coli, Mycobacterium tuberculosis, Candida albicans* and human.

EcDHFR structure shows preferential pathways for energy flow that enables coupling of hydration shell solvent with the active site. The informatics approach indicates that certain residues are better than others at communicating with neighboring residues. The list of top energy communicating residues includes Ala7, Ile14, Phe31 and Tyr100 which show the lowest hit times (as depicted in FIG. 13). In this informatics approach, hit time is a measure of time (in arbitrary units) that it takes each residue to communicate a message to its neighbors. Residues with lowest hit times therefore indicate residues that are most suitable at relaying long-distance communications. An overall inspection of the EcDHFR structure shows that the external loop shows low hit times while the internal residues show higher hit times. These residues with low hit times have been previously indicated to a part of conserved network of coupled motions. Although it is useful in identifying these residues that are suitable for long range communications in enzyme structures, the informatics approach does not provide insights into the biophysical mechanism of long-range connectivity.

The biophysical mechanism of long-range connectivity was tested by monitoring energy flow within the enzyme structure. Using the approach above where a temperature gradient is introduced to induce energy flow from one region of the molecular system to another, we monitored the flow of kinetic energy from the solvent to the active site residues. A small number of atoms in the active site were cooled (by scaling down the atomic velocities in molecular dynamics run periodically), while the entire system was kept at constant temperature of 300 K. The cooling of atoms in the active site is motivated by treating active site as a sink of energy, where the energy facilitates in overcoming the free energy of activation. With this temperature gradient in place during the hydride transfer reaction, the ability of residue pairs in enzyme-substrate to conduct kinetic energy was characterized. This allowed computation of energy connectivity of each residue in the protein. Higher values of the energy connectivity indicate that the residues are more suitable for conducting the kinetic energy from solvent on the enzyme surface into the active site.

Figure 14:
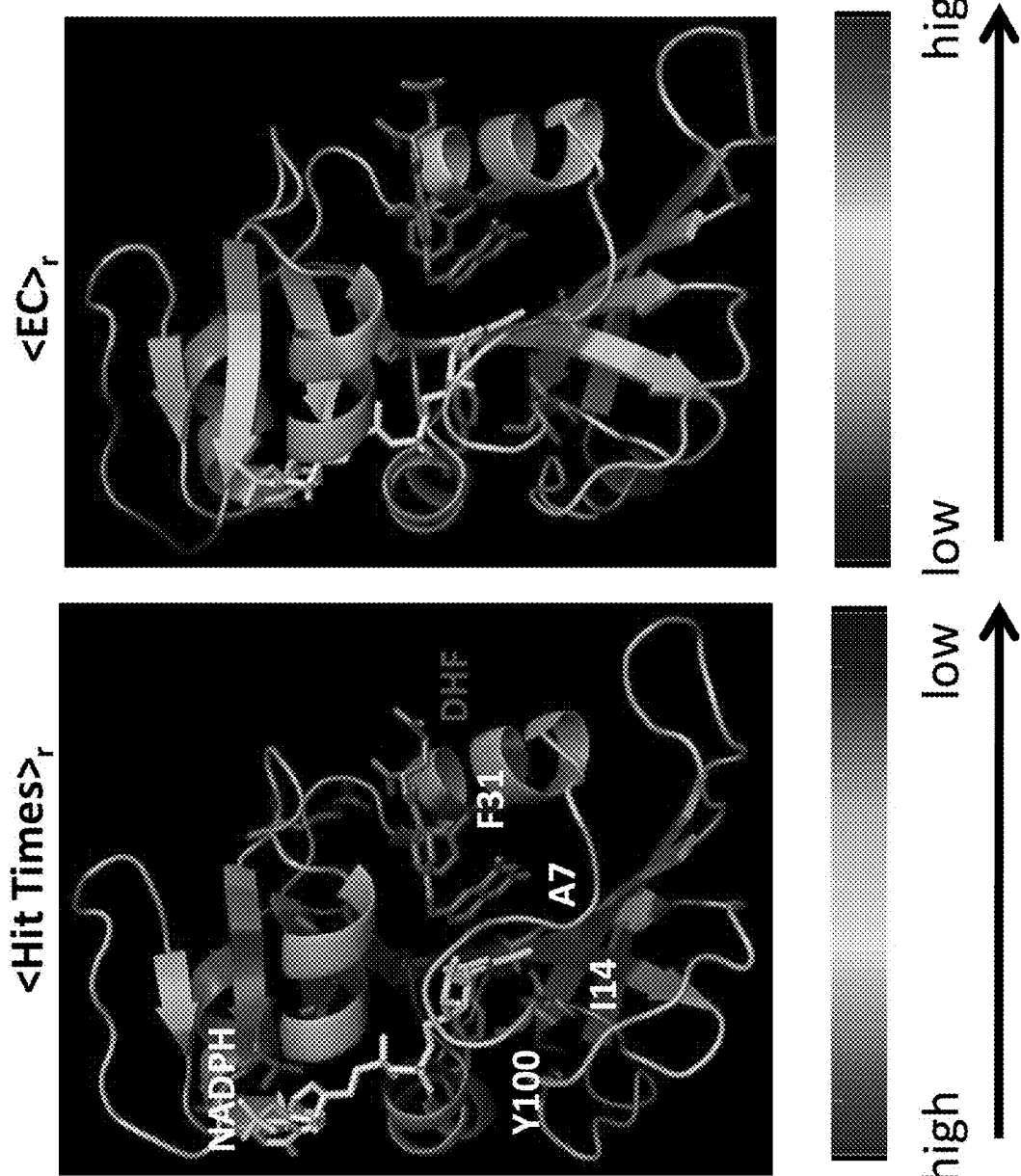
FIG. 14 depicts the hit times and energy conductance results for various residues of *E. coli* dihydrofolate reductase (EcDHFR).

These two approaches provide quantitatively similar results as depicted in FIG. 14. Correlation indicates that residues with low hit times are good at conducting energy. For EcDHFR, the residues with the best ability to conduct energy were the same as the ones that have been previously implicated in a network of coupled motions.

Figure 15:
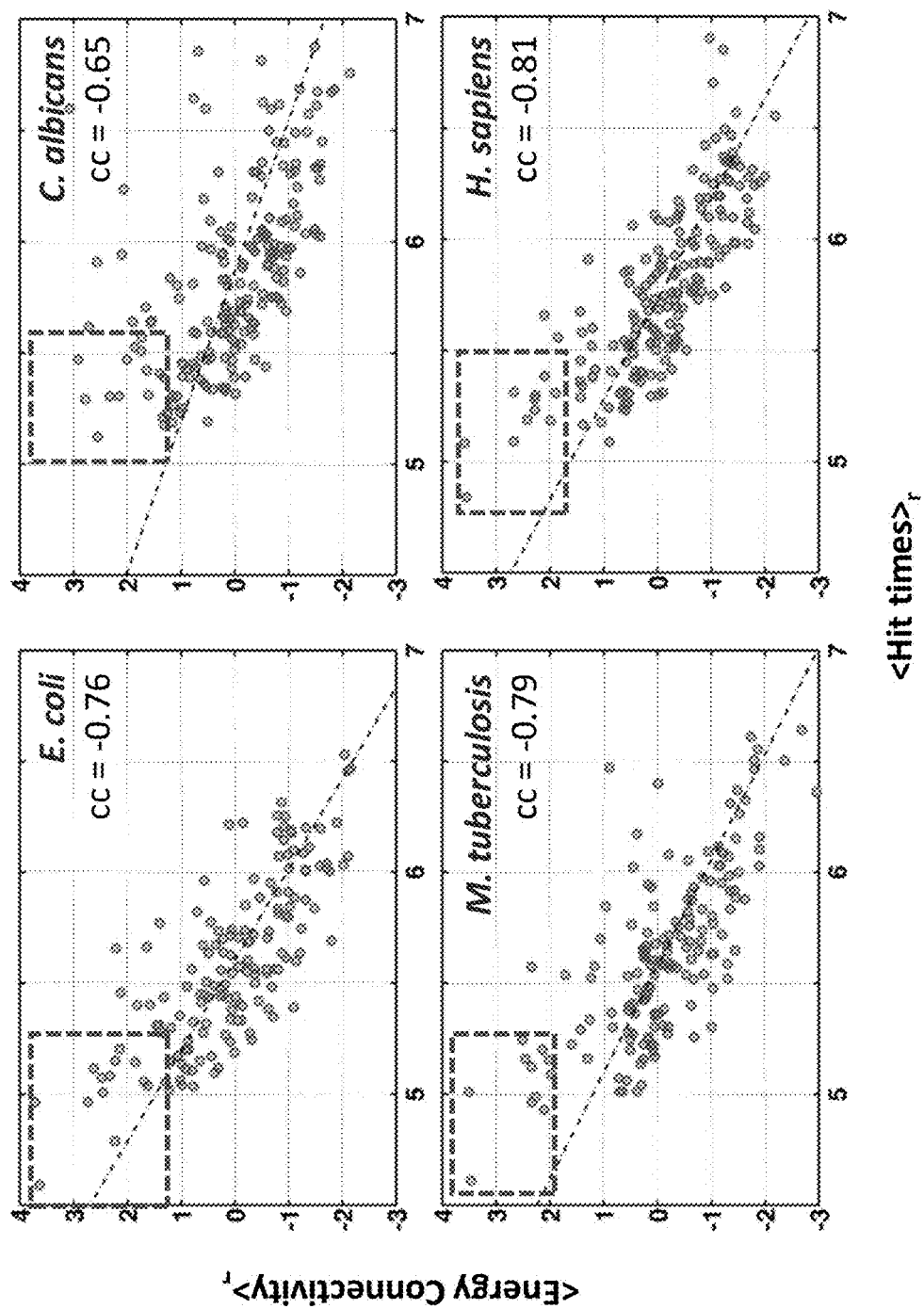
FIG. 15 shows the inverse correlation between hit time and energy conductance. Energy conductance is a measure of a residues ability to relay energy to its neighbors. The network residues (with low values of hit times and high energy connectivity) from DHFR are indicated with the dashed rectangle for each of the four species *Escherichia coli, Mycobacterium tuberculosis, Candida albicans* and human
Figure 16:
FIG. 16 depicts the results of the energy conductance for dihydrofolate reductase from the four species: *Escherichia coli, Mycobacterium tuberculosis, Candida albicans* and human. The arrows indicate the flow of energy from the surface to the active site.

Active site residues that participate directly in enzyme mechanism are known to be conserved; however, the role of conserved residues located distal to the active site still remains a mystery. Therefore, DHFR structures from the other 3 different species were examined using the same approaches (FIG. 15 and FIG. 16). Results indicate that the residues which are most suitable for long range energy connectivity are conserved across evolution. These 4 species share only 30% sequence similarity. It is important to note that the simulations used for computing energy connectivity were performed in non-equilibrium conditions as an artificial energy gradient was introduced by cooling the active site. The simulations used in the informatics approach were performed under equilibrium conditions, with no temperature gradient or any other constraints on the systems. Therefore, both of these approaches identifying the same residues provides confidence in the ability to characterize the residues for long range connectivity in proteins.

The results from the informatics and the biophysical approach can be summarized as follows. The enzyme structure shows presence of conserved residues, all the way from surface to the active site, that provides channels of long-range connectivity. The flow of energy from the surrounding solvent on the enzyme surface through these channels into the active site is the mechanism of the long-range connectivity. It has been hypothesized that this energy is required to overcome the activation energy barrier in the active site. The residues that form these conserved channels have been indicated to be part of conserved networks.

Further, these two approaches allow providing a quantitative score to each residue (hit time and energy connectivity) which is used to evaluate the ability of the residue to transfer energy from a surface of an enzyme to its active site of catalysis. Both of these approaches can assign quantitative scores to each residue for energy connectivity. Therefore, scores can be assigned to each allosteric site as well as the network residues connecting the allosteric site to the active site.

Determining Mechanisms of Already Known Allosteric Modulators

It is possible to find molecules that bind at distal sites of enzymes through high-throughput screening approaches. Carefully designed assays can indicate whether these molecules inhibit enzymatic activity through competitive or non-competitive inhibition. However, it is not easy to obtain the mechanism of allosteric inhibition once these molecules are discovered. To successfully take hit-compounds and develop them into lead compounds requires a detailed understanding of the mechanism of allosteric modulation of the discovered compounds.

The approach described here allows for investigation of the mechanism of allosteric modulation. In one embodiment, naturally known modulators, or those discovered through computational or experimental approaches, are used to computationally model the enzyme's activity without the modulator and in the presence of the modulator. For modeling the activity of the enzyme, a suitable reaction coordinate (or a plural of reaction coordinates) is used to appropriately describe the protein's activity of interest (i.e. catalysis).

Conformational data collected either from molecular dynamics simulations or other experimental approaches can be used to deconvolute the conformational landscape. Such experimental approaches can include NMR experiments or X-ray crystallography. This can be performed when modulator is absent and separately when the modulator is bound at the known location. As described in Example 1, the conformational sub-states and conformational transitions associated with the functionally relevant sub-states can be identified computationally.

Once identified, the populations can be compared in the functionally relevant sub-states and the regions showing large dynamical flexibility and changes in electrostatic properties of various protein regions can also be compared. A decrease in the number of conformations in the functionally important sub-states of a protein implies that the activity of the protein would be decreased, or the function would be inhibited. Modulators that cause this decrease are negative allosteric modulators. The conformational changes in the molecule associated with the important conformational sub-states would also provide mechanistic insights, associated with changes in critical interactions, distances and angles between the important atoms in the active site.

In addition, the comparison of QAA characterized conformational sub-states will also provide additional information, such as the possibility of other allosteric sites.

Example 3

Mechanism of PS48 Modulation of PDK1

A small molecule, PS48, is known to act as an allosteric modulator of phosphoinositide-dependent protein kinase 1 (PDK1). However, the crystal structure of PDK1 in the presence and absence of PS48 are essentially the same (see FIG. 17). Therefore, the mechanism of how PS48 acts as an allosteric modulator of PDK1 was unknown.

The methodology described here quantitatively predicts the mechanism of PS48 action. Molecular dynamics simulations were used to sample the reaction pathway associated with the kinase activity of PDK1. The kinase activity involves the transfer of a phosphate group on to a substrate peptide. The simulations were based on a model from another kinase structure, protein kinase A. Three states were modeled for reactant, transition state and product with umbrella sampling, based on previous computational studies of kinase mechanisms. A description of reaction coordinates based on bonds breaking and forming described previously were also used. A total of 10,800 conformations for each system were used for further analysis.

Figure 17:
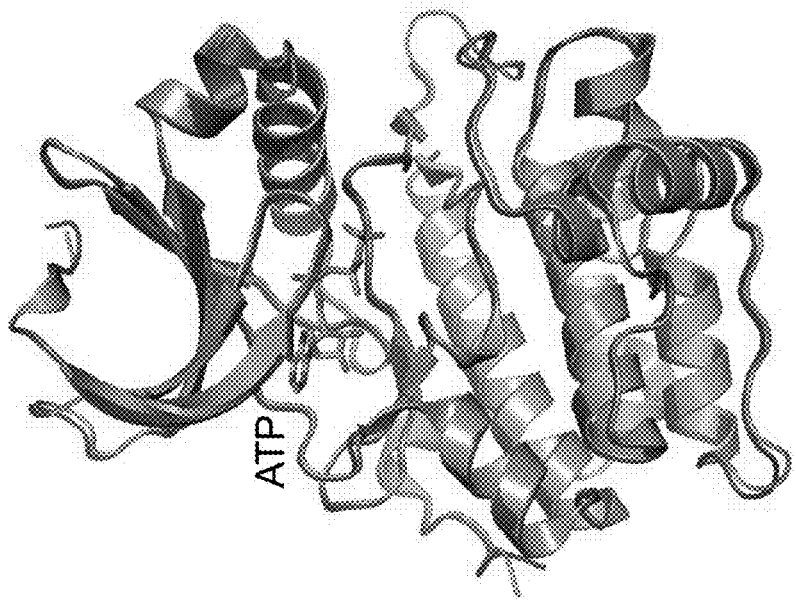
FIG. 17 depicts the binding position of small molecule (PS48) on the phosphoinositide-dependent protein kinase 1 (PDK1), left panel. The right panel shows lack of structural difference in presence (red structure) and absence (gray) of PS48 in the allosteric site.
Figure 17:
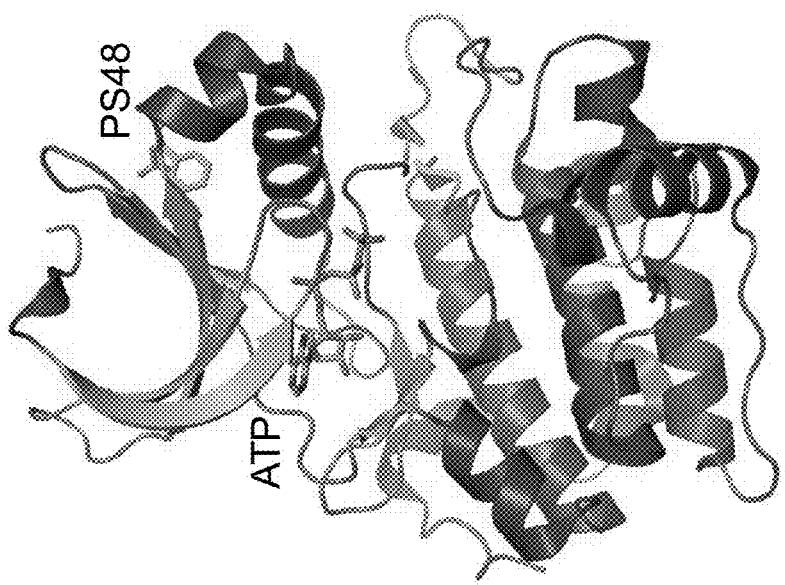
Figure 18:
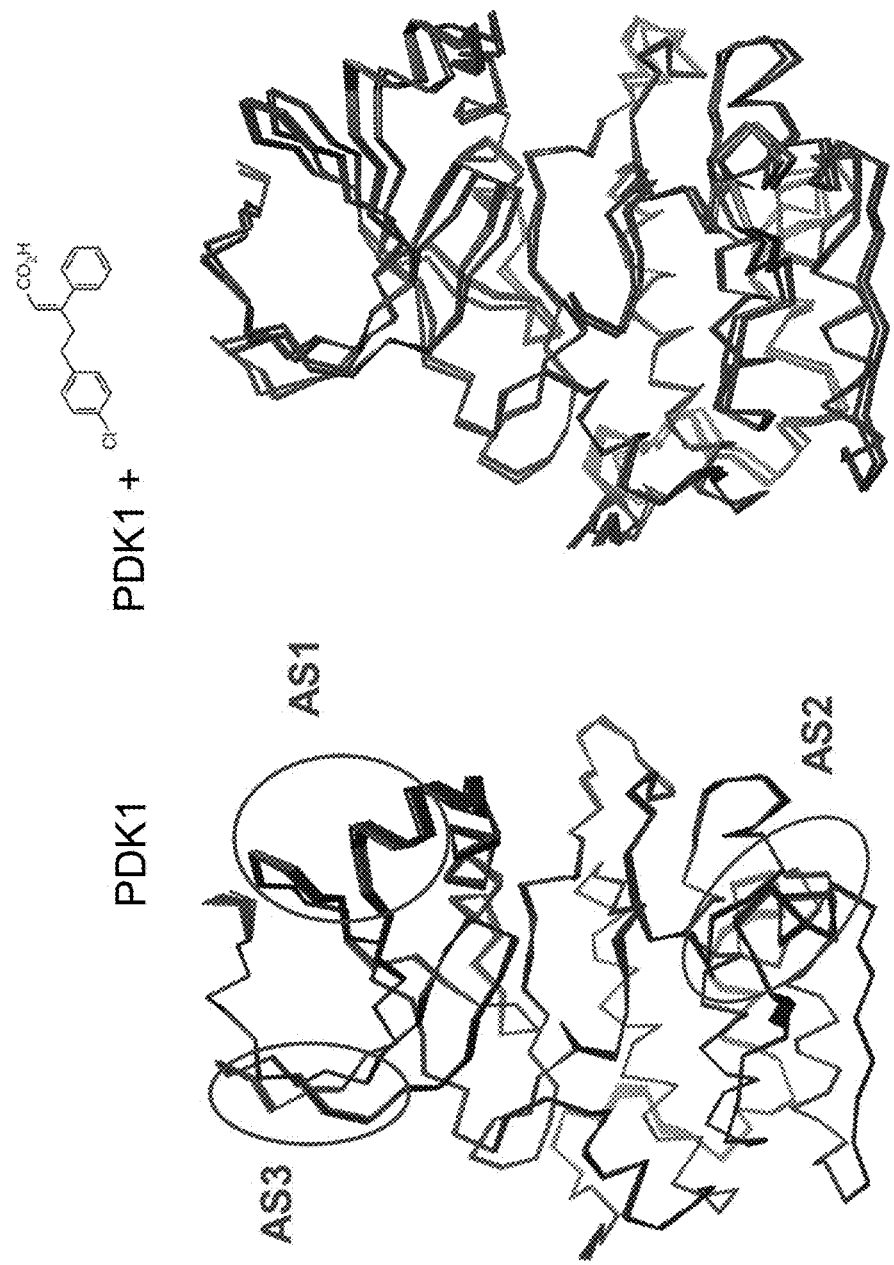
FIG. 18 depicts the identification of allosteric sites of PDK based on the conformational changes associated with the kinase activity. On the left side, the identified sites show most significant conformational changes in QAA are marked with red ellipses as AS1, AS2, AS3. On the right side, the conformational changes associated with PDK1 kinase activity are shown in presence of PS48. The chemical structure of PS48 is also depicted.

The results of molecular dynamics simulations were characterized with QAA. The results allow identification of the conformational sub-states associated with the reactant (R), product (P) and transition state (TS) for the case of PDK1 enzyme without any modulator and separately with the modulator PS48 presented in the PIF pocket, as depicted in FIG. 17-18. PS48 binds away from the ATP binding site of the PDK1 kinase, and is therefore an allosteric modulator.

Figure 19:
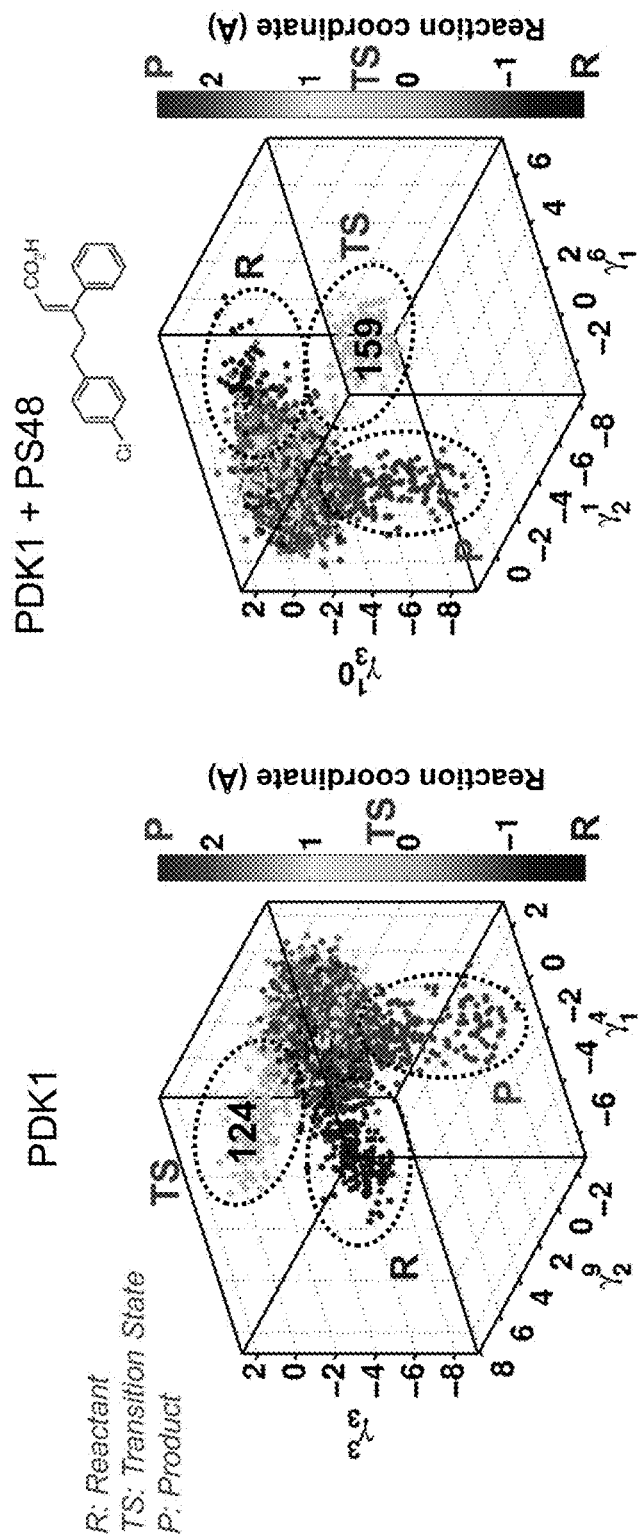
FIG. 19 depicts the results identifying the allosteric sites related to conformational sub-states of PDK1 kinase activity and the mechanism of action for PS48 on PDK1 kinase activity. The left panel shows conformational sub-states identified for the kinase activity of PDK1. The right panel shows conformational sub-states when PDK1 is in the presence of PS48.
Figure 20:
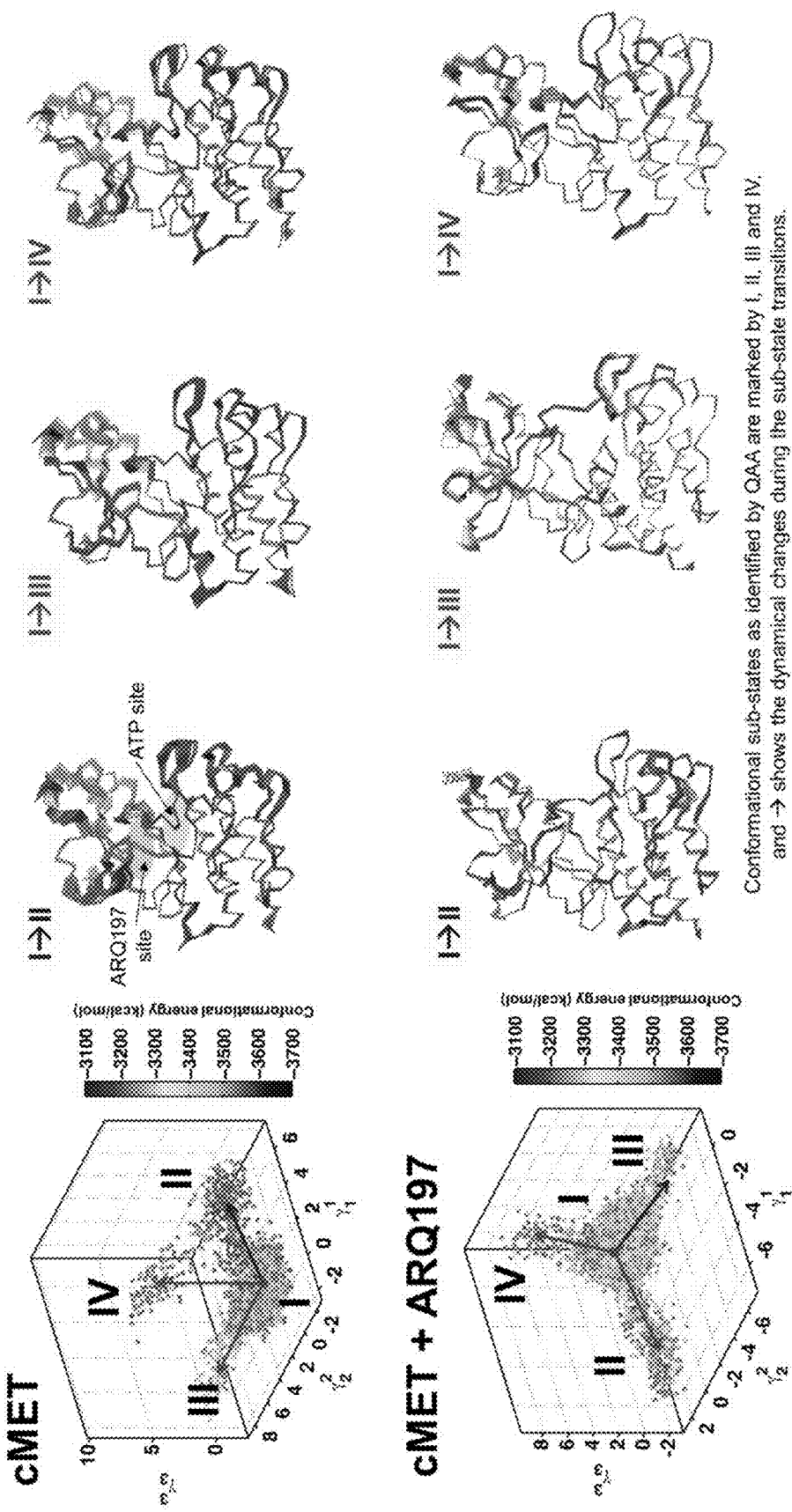
FIG. 20 depicts the mechanism of action of ARQ197 on tyrosine kinase human mesenchymal-epithelial transition factor (cMET) with conformation sub-states as identified by QAA.

The results from QAA are depicted in FIG. 19-20, which shows the functionally important sub-states associated with the transition state (TS) identified. The identified conformational sub-states show reactant (R), transition state (TS) and product (P) sub-states. Note that here the TS is defined with the reaction coordinate value of 0, where the bonds breaking and forming are close to half way complete.

The QAA indicates in FIG. 19 that when the modulator PS48 is present in the allosteric site, the number of conformations in the TS sub-states increases to 159, as compared to 124 in case of enzyme without the modulator. Therefore, PS48 enables more conformations to reach the transition-state through the conformational activation mechanism. According to the energetic scheme illustrated in FIG. 3, PS48 therefore serves as a positive allosteric modulator.

More importantly, the computational approach provides insights into the mechanism of allosteric modulation. Similar to the case of cyclophilin A described in Example 1, the characterization of the conformational changes associated with the protein transition from the ground state to TS sub-states, allowed identification of the regions showing large flexibility. As depicted in FIG. 18, a number of regions in the native enzyme (without the PS48 modulator) are active. These three regions are marked by red ellipses in the left panel of FIG. 18. It is hypothesized that these regions are dynamically active and play an important role in coupling of the surrounding environment to the kinase activity. The presence of PS48 in the PIF pocket makes the enzyme even more conformationally active, as shown in the right panel. This provides insights into how more conformations are able to reach the higher energy TS sub-state. In contrast to the case of PS48 in PDK1 PIF pocket, other modulators which make the conformations more rigid and reduce the conformational changes in functionally important regions.

In addition to providing insights into the mechanism of PS48's modulation of PDK1, the conformational methodology allows identification of the allosteric sites on PDK1. Taking a closer look at the results of the enzyme (without the modulator) QAA results identifies the regions that show large conformational changes associated with the transitions into the functionally important TS sub-state. The 3 most important regions are marked in FIG. 18 with red ellipses. These regions are designated as potential allosteric sites. When ranked by the degree of flexibility, the PIF pocket emerges as the most relevant allosteric site. Therefore, it is no coincidence that the modulator PS48 binds to this region and is able to modulate the activity of PDK1.

Example 4

Mechanism of ARQ197 Non-Competitive Inhibition of cMET Kinase

Tyrosine kinase human mesenchymal-epithelial transition factor (cMET) is a commonly targeted kinase for cancer therapies because the cMET signaling pathway is frequently dysregulated in human cancers. cMET has an activation loop (A-loop), which is an extremely flexible portion of the kinase that can exist in multiple conformations.

An allosteric modulator of cMET has been identified that selectively stabilizes the A-loop in such a way that the kinase adopts an auto-inhibited conformation. This allosteric modulator, Tivantinib/ARQ197 selectively inhibits cMET for treatment of lung cancer. However, Tivantinib/ARQ197 causes unwanted side effects and is not very effective. Therefore, methods of identifying improved allosteric modulators is needed. A systematic approach to the characterization of the cMET kinase was used to identify allosteric sites and generate hit-compounds for these sites.

First, allosteric sites associated with cMET active-inactive state conformational transitions were identified. MD simulations were used to sample the conformational landscape of cMET. The cMET kinase was modeled in active and inactive forms. The major difference between these two states is in the conformational sub-states that are sampled by the protein. Microsecond timescale simulations were used to identify the conformational sub-states sampled by these two states, and the resulting information was used to identify distal regions that control the sampling of the sub-states. The results of these calculations are shown in FIG. 20.

The conformations were analyzed through a software platform for characterizing the active-inactive conformational transitions. The cMET regions showing the largest motions between the active and inactive states and within each state were identified and quantitatively characterized. Results shown in FIG. 20 identify regions of interest.

Then, the potential allosteric sites of cMET were ranked. The allosteric sites identified on the basis of conformational sub-states associated with active-inactive state transitions were ranked for impact on cMET activity. The ranking was based on quantitative scores indicating the impact of each site on the target activity modulation.

Figure 21:
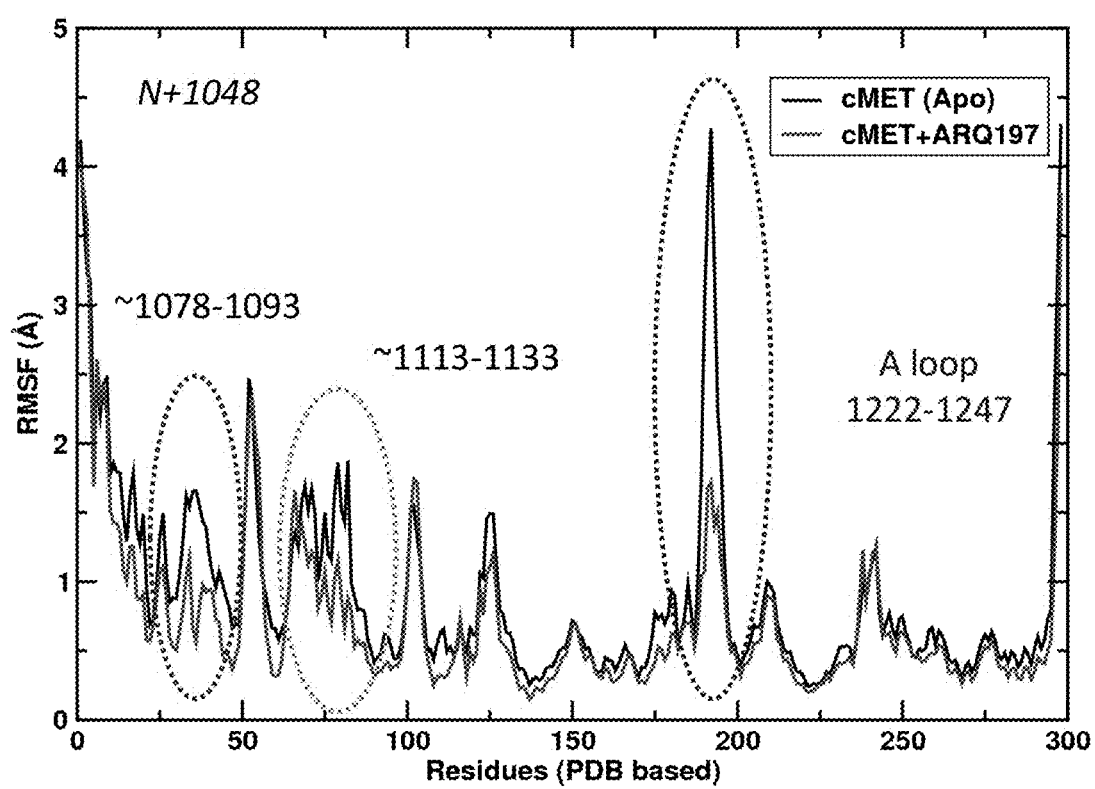
FIG. 21 depicts the changes in dynamical flexibility (characterized with root-mean-square fluctuations (RMSF)) between cMET with and without ARQ197.

As shown in FIGS. 20-21, a number of regions show high flexibility while cMET is in active state, but binding of ARQ197 reduces or even completely eliminates the flexibility of these regions. Allosteric sites were ranked based on characterization of a pathway of energy connectivity between the allosteric sites and the active site (namely, the ATP-binding pocket for cMET). This amounts to quantifying the energy flux through the network channels or the energy flow from the allosteric sites to the active site.

Prediction of Allosteric Sites and Discovery of Allosteric Modulators at these Sites In another embodiment, allosteric sites of proteins can be discovered even where no previous information exists about the availability of modulators or the locations of allosteric sites. Using the approaches (and combinations thereof) described above in Examples 1-4, the activity of protein targets such as enzymes can be modeled using computational methods. The biophysical data can be obtained from experimental techniques including one or more of nuclear magnetic resonance (NMR), X-ray crystallography, cryogenic electron microscopy (Cryo-EM), neutron scattering, and hydrogen-deuterium exchange.

The information collected from experimental studies or modeled with computational methods can then be used to identify conformational sub-states associated with various stages of the protein's activity of interest. For example, in the case of $NAD^+/NADP^+$ binding enzymes, these are conformations associated with the rate limiting event of the enzyme such as binding of substrate or cofactors, release of substrate or cofactors, or hydride transfer. Similarly, in the case of kinases these are conformations associated with the binding of substrate or cofactors, release of substrate or cofactors, or the phosphoryl transfer step.

Once the information is obtained, the QAA states are analyzed. Regions showing large amounts of conformational flexibility are identified as potential allosteric pockets. Further analysis is performed for the coupling of energy transfer from the sites into the active sites to rank the potential allosteric sites. Using the method described above, the hit times and conductance values were calculated for each protein residue in the allosteric site as well as each protein residue within the network that connects these potential allosteric sites to the active site. Each of these potential allosteric sites is assigned a score and/or ranking based on the results of the energy coupling efficiency.

A library of compounds is computationally screened against the potential allosteric sites to find hit compounds. This can be performed with high throughput computational docking software. Alternatively, molecular dynamics or energy minimization or Monte Carlo methods are used to identify compounds that bind to the target protein with moderate to high affinity. A subset of compounds scoring well is identified.

The high scoring compounds from the computational screening are inspected for their impact on the conformation populations (as described in Examples 3 and 4). The discovered hit compounds are modified based on the knowledge of the allosteric site structure to improve the interaction between the protein residues and chemical compound by modification of the functional groups of the compound. The effect of the modified compound on the protein activity is evaluated computationally as well as experimentally.

Example 5

Predicting Allosteric Sites for Protein Kinase A

Figure 22:
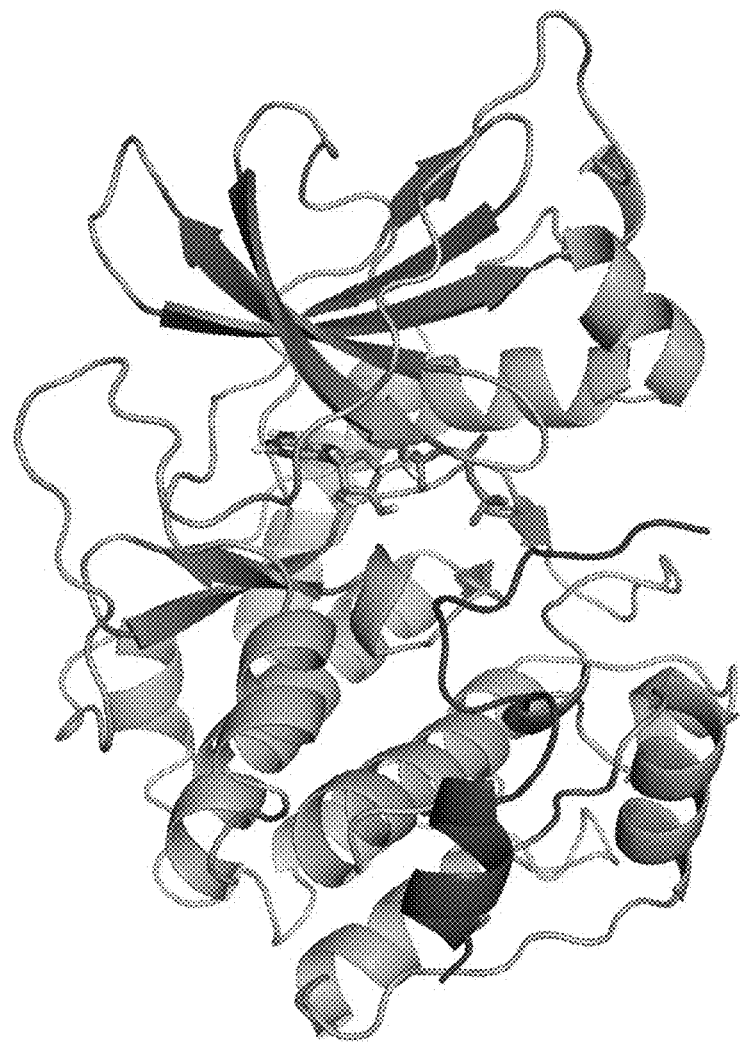
FIG. 22 depicts the protein kinase A (PKA). The ATP is shown in sticks (red-green-blue) to identify the ATP binding pocket and a binding protein/substrate peptide is shown in red.

Predicting allosteric sites of a protein where there is no previous information regarding allosteric sites or allosteric modulators is done with the approaches described in Example 2. For example, for protein kinase A, molecular dynamics simulations in combination of umbrella sampling simulations were used to model the kinase activity (using an approach similar to the PDK1 described above). The starting structure for protein kinase A (PKA) is depicted in FIG. 22.

Figure 23:
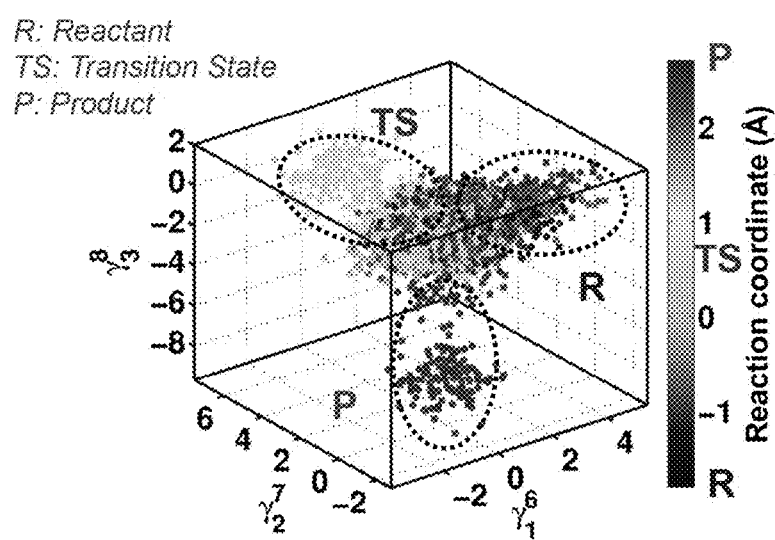
FIG. 23 depicts the conformational sub-states associated with the PKA kinase activity identified using QAA. The conformational sub-states are identified using the value of reaction coordinate, for reactant (R), transition state (TS) and product (P) sub-states.
Figure 24:
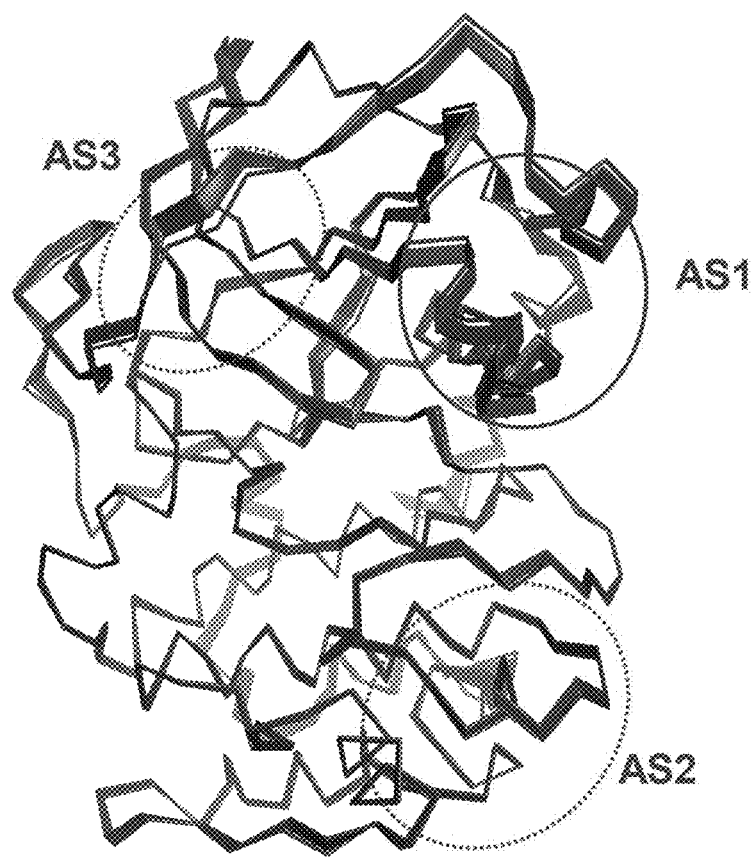
FIG. 24 depicts the conformational change associated with the PKA conformational transition into the TS sub-state. The regions showing the most significant conformational changes in QAA are marked with red ellipses as allosteric sites AS1, AS2, AS3.

The results identify conformational sub-states and the TS sub-state associated with the phosphoryl transfer mechanism as depicted in the QAA graph of FIG. 23. The conformational transition into the TS sub-state is depicted in FIG. 24. This figure identifies the 3 primary regions that are potential allosteric sites of PKA.

Example 6

Discovery of Hit Compounds for PDK1 by Virtual Screening

Figure 25:
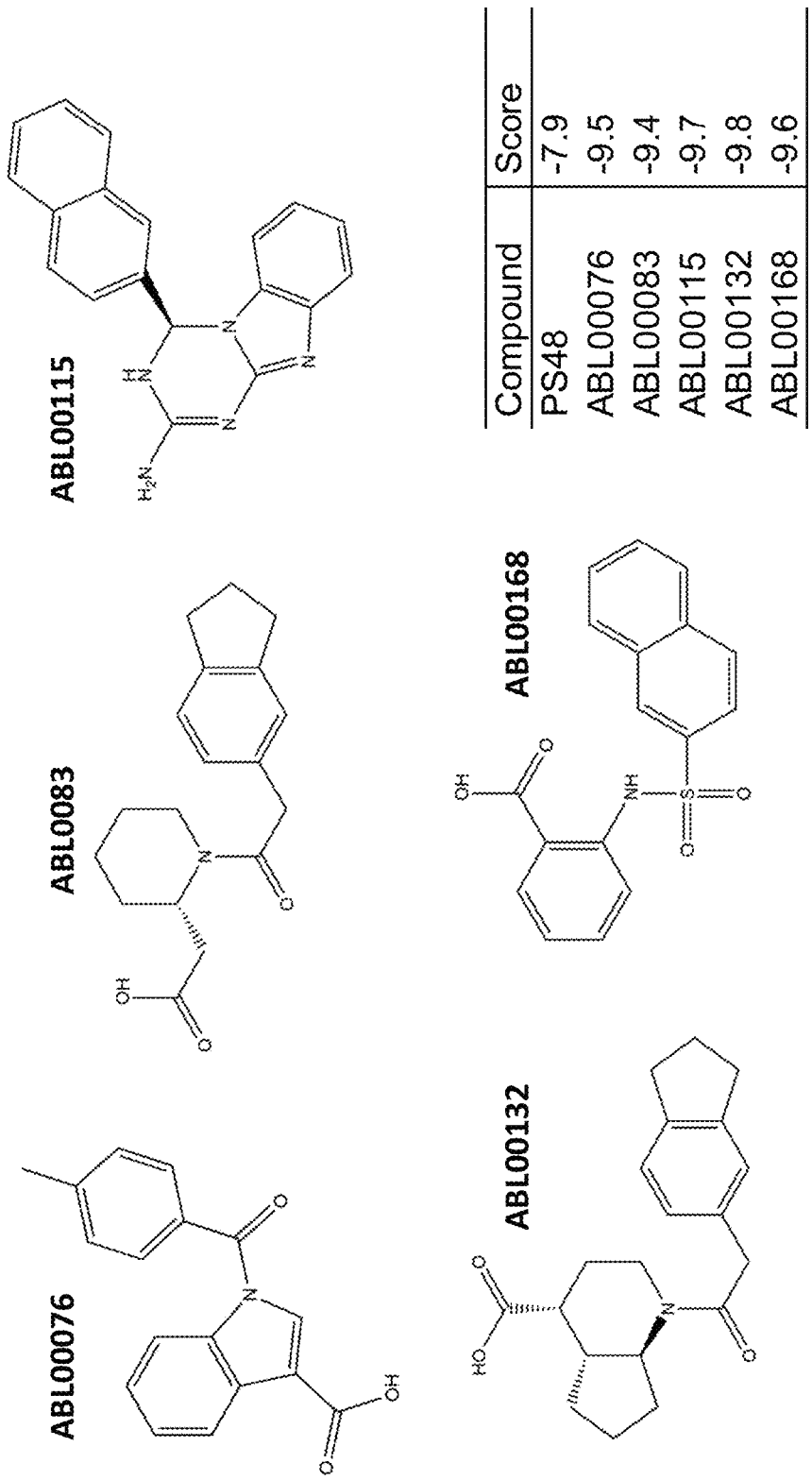
FIG. 25 shows the structure of 5 best scoring compounds on allosteric site 1 of PDK1. The binding affinity score for these compounds and comparative value for the PS48 is provided in the table.

The discovered allosteric sites for PDK1 were used to virtually screen compounds for discovery of hit compounds. A sub-set of ZINC virtual compounds library consisting of 1.2 million compounds were used in the screening. These compounds are typically available from various vendors and have similar properties to many lead compounds. The calculations were performed using AutoDOCK Vina software. The results for the 5 top-most hits are depicted in FIG. 25 for the allosteric site 1 (AS1, the PIF pocket).

One of the concerns regarding the allosteric sites discovered through the described approach is that they consist of flexible loop areas that show large dynamical changes. It can be difficult to find chemical compounds that bind well to these regions. As the results indicate in FIG. 25, the listed 5 compounds show improved binding scores when compared to known modulator PS48. The predicted binding affinity for PS48 by the docking program is −7.9 kcal/mol, while all the 5 compounds indicate better binding as the affinity is in −9.4 kcal/mol or higher.

Figure 26:
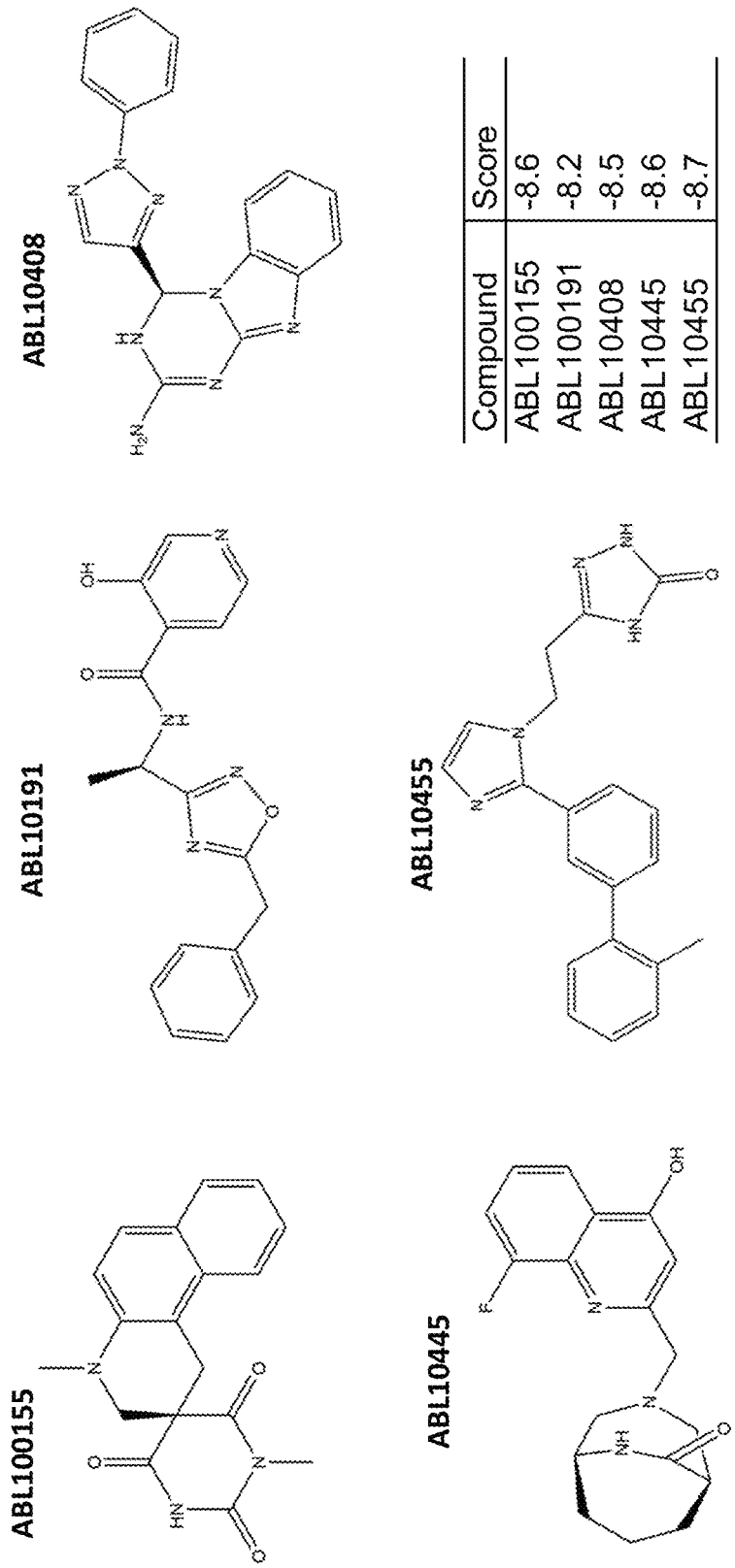
FIG. 26 shows the structure of 5 best scoring compounds on allosteric site 2 of PDK1. The binding affinity score for these compounds is provided in the table.

Further, the allosteric site 2 (AS2) was also screened against 1.2 million compounds. The results are depicted in FIG. 26, which shows a predicted binding affinity of −8.2 kcal/mol and higher.

Example 7

Figure 27:
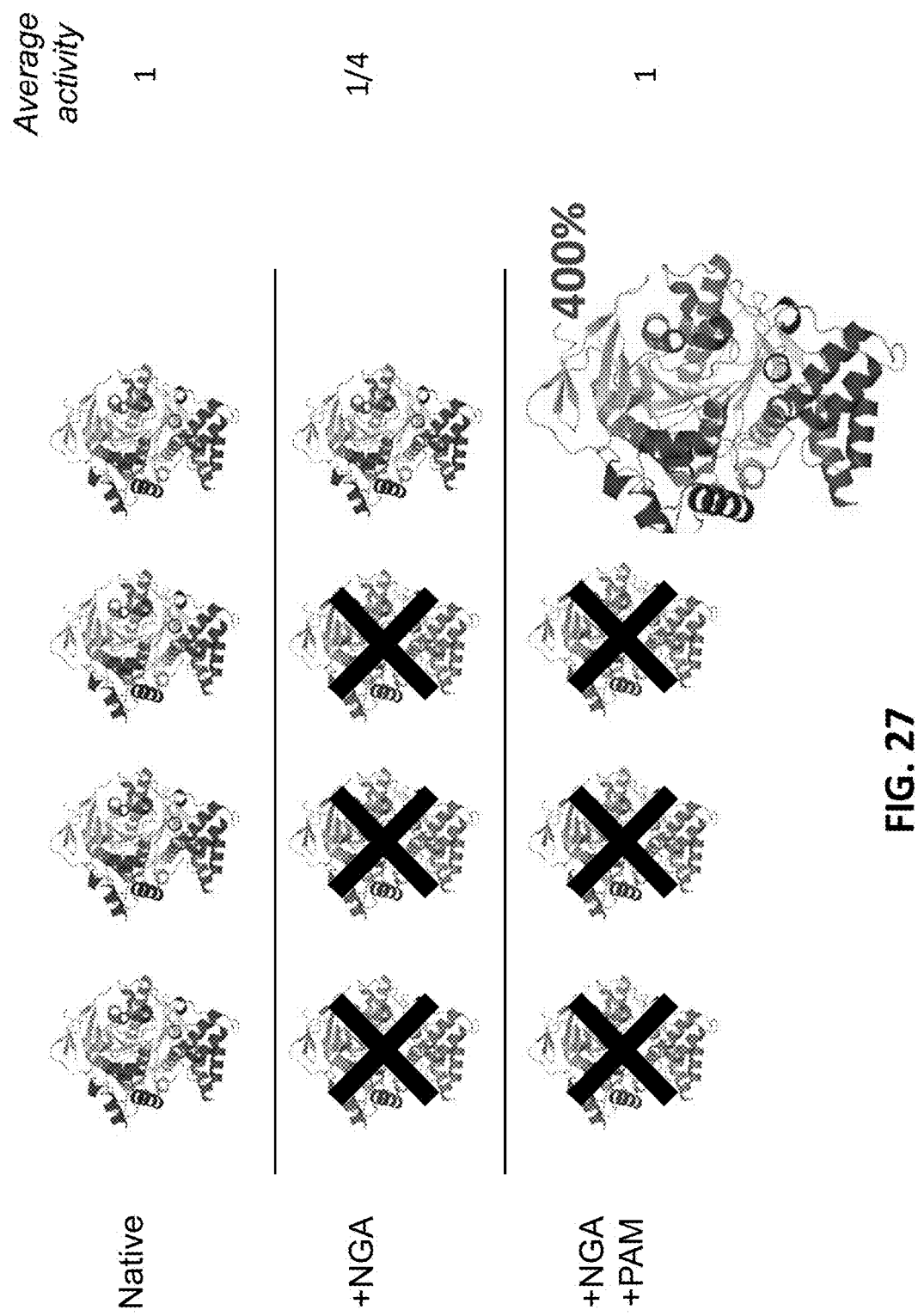
FIG. 27 shows the approach of using a PAM to treat the loss in activity of enzyme acetylcholinesterase (AChE) under exposure of a nerve gas agent (NGA). Different NGA molecules attack and destroy the activity of AChE by covalent binding. In the example shown, in cases where 75% of AChE molecules completely lose activity under NGA exposure can be effectively treatment by a PAM, which improves the enzyme activity of remaining AChE molecules to 4 times (or 400%) of the native enzyme.

Discovery of Allosteric Sites of Human Acetylcholinesterase and Design of PAMs for Human Acetylcholinesterase The enzyme human AChE is targeted by nerve gas agents (NGAs) such as organophosphates. AChE is an important enzyme involved in signal transduction between nerves and therefore the impairment of the enzyme due to NGAs has an immediate impact on muscle function. The mechanism of NGA involves irreversibly inactivating the AChE enzyme by forming a covalent bond with the active-site residue. Among other strategies one of the treatments being considered is development of a PAM that improves the function/turnover by several folds. The benefit of this strategy is that in case of exposure to NGAs the administration of PAM based drug would rescue the activity. For example, as shown in FIG. 27 if NGA destroys 75% AChE activity then a PAM that improves activity of the remaining functioning AChE molecule by 4-folds would completely rescue AChE's physiological functions.

Molecular dynamics simulations were used to model the AChE activity. Three states were modeled for reactant, transition state and product with umbrella sampling, based on previous computational studies of AChE mechanism. A description of reaction coordinate based on bonds breaking and forming described in the previous study was also used. A total of 15,000 conformations for each system were used for further analysis.

Figure 28:
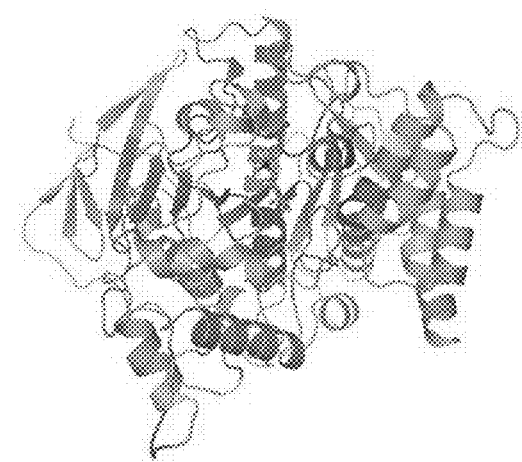
FIG. 28 depicts the identification of allosteric sites for enzyme AChE. The left most panel shows the results of QAA for the identification of transition states (TS) conformational sub-states, $TS^1$ and $TS^2$. Similar to the cases of PDK1 and cMET, the conformational transition into these sub-states (shown in middle panel) were used to identify allosteric sites, AS1-AS3. The orientation of enzyme is shown in the right most panel with substrate in the active site.
Figure 28:
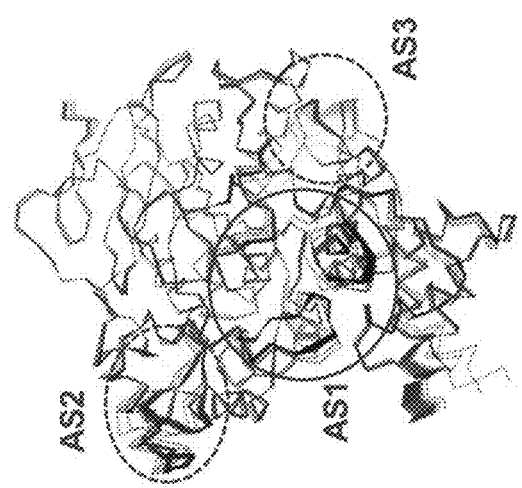
Figure 28:
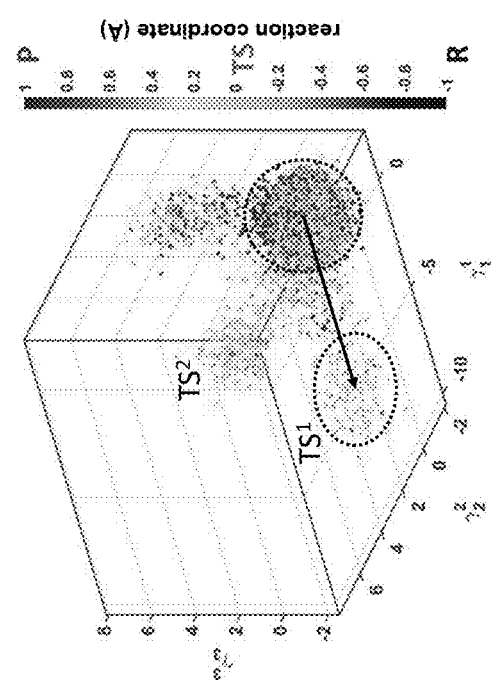

The results of molecular dynamics simulations were characterized with QAA. The results allow identification of the conformational sub-states associated with the reactant (R), product (P) and transition state (TS) for the case of enzyme without any modulator. The results depicted in FIG. 28, identified potential allosteric sites AS1, AS2 and AS3. These results from QAA identified the conformational fluctuations of enzyme enabled the access to two conformational sub-states $TS^1$ and $TS^2$. The conformational transitions from the ground state with mixed conformations into the primary TS cluster ($TS^1$) is depicted in the middle panel. The additional TS sub-state $TS^2$ was also identified by QAA. The protein regions which show the largest movements in the conformational transitions into the $TS^1$ and $TS^2$ were characterized as the allosteric sites AS1-3.

Figure 29:
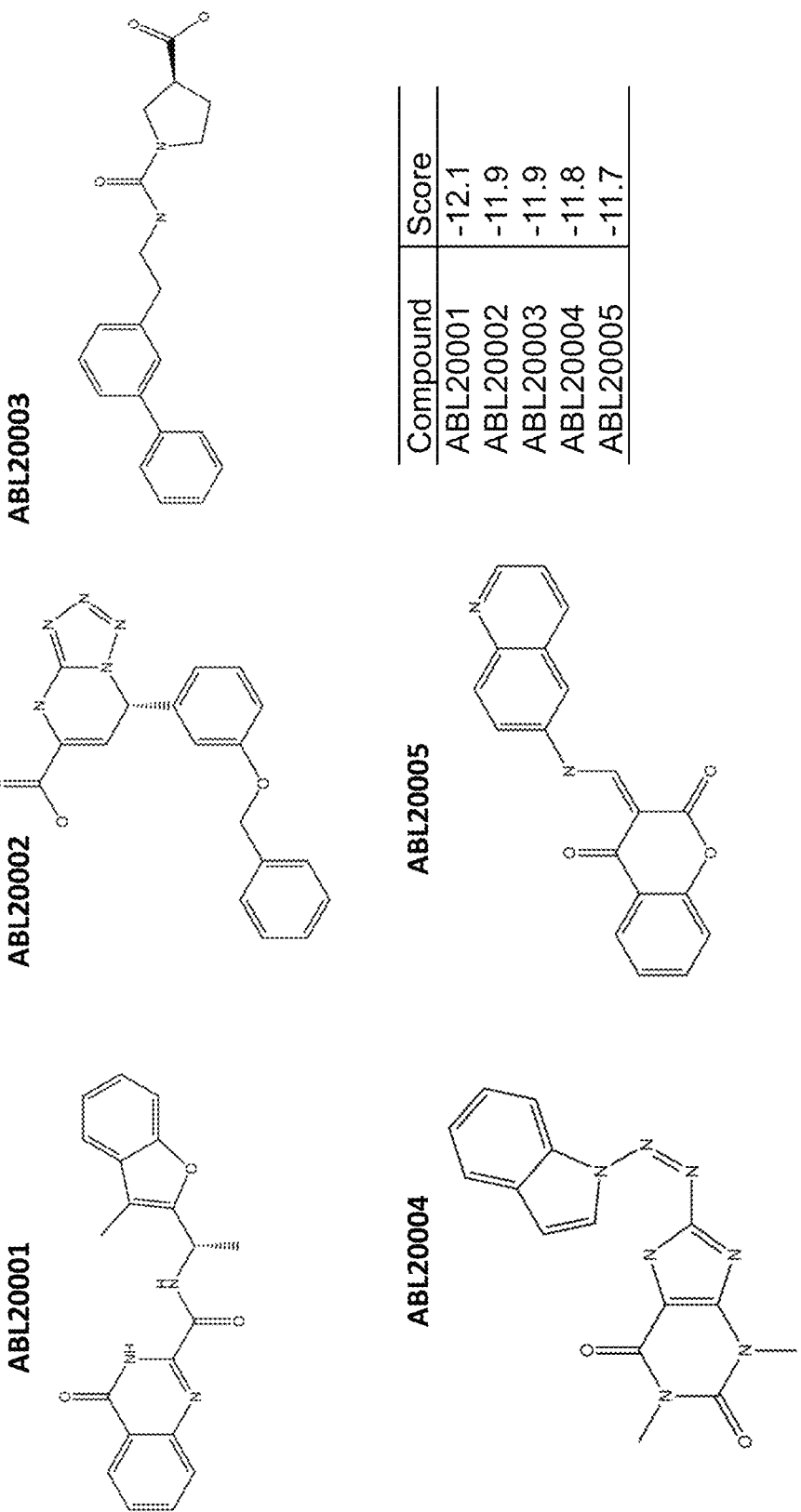
FIG. 29 depicts compounds identified that bind to the identified allosteric site AS1 of AChE. The scores from docking are listed.

Based on the discovery of the allosteric sites, virtual screening on 1.2 million compounds were performed on these sites for discovery of the compounds. These compounds are typically available from various vendors and have similar properties to many lead compounds. The calculations were performed using AutoDOCK Vina software. A number of compounds have been identified and investigated for PAM activity. The results for the 5 top-most hits are depicted in FIG. 29 for the allosteric site 1. The docking scores range from −11.7 to −12.1 kcal/mol.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method of identifying positive allosteric modulators of a target enzyme, the method comprising:
   accessing biophysical and dynamics data for the target enzyme;
   analyzing, with a computing system, the biophysical and dynamics data to identify one or more potential allosteric sites located on a surface remote from an active site of the target enzyme, the potential allosteric sites comprising a plurality of residues energetically coupled to the active site through an energy transfer network of residues within the target enzyme;
   quantifying a level of energy flow through the energy transfer network between each of the one or more potential allosteric sites and the active site;
   scoring each of the potential allosteric sites based on druggability and quantity of energy flow from an allosteric site to the active site;
   selecting one or more of the potential allosteric sites having the best scores to produce a subset of allosteric sites;
   computationally screening a plurality of chemical compounds to determine a binding energy between each of the subset of allosteric sites and each of the plurality of chemical compounds;
   selecting a subset of the plurality of chemical compounds having a best binding energy as compared with the binding energy of a remainder of the plurality of chemical compounds;
   computationally modeling the subset of chemical compounds with different functional groups to produce modified chemical compounds with improved binding energy between the chemical compounds and the allosteric sites;
   computationally modeling the effect of the chemical compounds binding to each of the plurality of allosteric sites on the enzymatic activity of the target enzyme;
   quantifying each of a plurality of conformations of the target enzyme while bound to the chemical compounds and while not bound to the chemical compounds, the plurality of conformations including at least one conformational sub-state associated with increased enzymatic activity of the target enzyme;
   ranking the chemical compounds based on ability to modify the conformation of the target enzyme to enhance enzymatic activity by increasing energy flow from an allosteric site to the active site and increasing conformations in the sub-state associated with enzymatic activity;
   outputting a subset of top ranking chemical compounds as allosteric modulators for the target enzyme; and
   validating one or more of the subset of top ranking chemical compounds for use as a positive allosteric modulator for the target molecule using one or more of the following in vitro techniques: spectrophotometric assays, radiometric assays, mass spectrometry, multiple injection method studies, isothermal titration calorimetry studies, stopped-flow kinetics, steady state kinetics, or pre-steady state kinetics measurements.

2. The method of claim 1, further comprising receiving input at a user interface of a computing device to select the target enzyme.

3. The method of claim 1, wherein the biophysical and dynamics data is accessed from an enzyme data store in communication with the computing system.

4. The method of claim 1, wherein the biophysical and dynamics data is obtained by computational analysis of internal movements of the target enzyme that affect its enzymatic activity.

5. The method of claim 4, wherein the computational analysis is performed using quasi-anharmonic analysis (QAA).

6. The method of claim 1, wherein the biophysical and dynamics data is obtained by one or more of nuclear magnetic resonance (NMR), X-ray crystallography, cryogenic electron microscopy (Cryo-EM), neutron scattering, hydrogen-deuterium exchange, and computer simulations.

7. The method of claim 1, wherein criteria defining druggability include shape, weight, and charge of the binding site.

8. The method of claim 1, wherein the computational screening is performed using docking software.

9. The method of claim 1, wherein the computational modeling is performed using high-throughput computational docking software.

10. The method of claim 1, wherein quantifying a level of energetic coupling comprises performing molecular dynamics simulations to monitor the energy flow between residues within the target enzyme either by creating a temperature gradient or by adding extra kinetic energy at different surface sites of the target enzyme.

11. A system for identifying positive allosteric modulators of enzymes, the system comprising:
a processing device;
an enzyme database; and
a memory device in communication with the processing device, the memory device comprising instructions that, when executed by the processing device, cause the system to:
receive, at a user interface, input selecting an enzyme;
access biophysical dynamics data for the enzyme from the enzyme database;
analyze the biophysical dynamics data to identify one or more potential allosteric sites located remote from an active site of the enzyme, the potential allosteric sites being energetically coupled to the active site through an energy transfer network within the enzyme;
quantify a level of energetic coupling between each of the one or more potential allosteric sites and the active site of the enzyme;
score each of the potential allosteric sites based on suitability as a druggable site;
select one or more of the potential allosteric sites having the best level of energetic coupling and suitability as a druggable site to produce a subset of allosteric sites;
computationally screen a plurality of chemical compounds to determine a binding energy between each of the subset of allosteric sites and each of the plurality of chemical compounds;
computationally model the effect of the chemical compounds binding to each of the plurality of allosteric sites;
quantify each of a plurality of conformations of the enzyme while bound to the chemical compounds and while not bound to the compounds, the plurality of conformations including at least one conformational sub-state associated with increased enzymatic activity of the target enzyme; and
present the quantification results on the user interface; and
validate one or more of the subset of top ranking chemical compounds for use as a positive allosteric modulator for the target molecule using one or more of the following in vitro techniques: spectrophotometric assays, radiometric assays, mass spectrometry, multiple injection method studies, isothermal titration calorimetry studies, stopped-flow kinetics, steady state kinetics, or pre-steady state kinetics measurements.

12. The system of claim 11, wherein the memory device further comprises instructions that, when executed by the processing device, cause the system to:
identify one or more potential chemical compounds capable of binding to one of the ranked allosteric sites of the enzyme and positively modifying the enzyme's activity by increasing energy flow from an allosteric site to the active site and increasing conformations in the sub-state associated with enzymatic activity; and
store the one or more potential chemical compounds in a positive allosteric modulator data store.

13. The system of claim 12, wherein the one or more potential chemical compounds are selected from a chemical library.

14. The system of claim 11, wherein quantifying a level of energetic coupling comprises performing molecular dynamics simulations to monitor the energy flow between residues within the target enzyme either by creating a temperature gradient or by adding extra kinetic energy at different surface sites of the target enzyme.

15. The system of claim 14, wherein the conformations of the enzyme associated with the increased enzymatic activity are determined using one or more of root-mean-square-fluctuations (RMSF) analysis, principal component analysis (PCA), normal mode analysis (NMA), time-averaged normal coordinate analysis (TANCA), quasi-harmonic analysis (QHA), and quasi-anharmonic analysis (QAA).

16. The system of claim 11, wherein the effect of each compound on protein activity is scored with changes in conformational sub-states.

17. The system of claim 16, where the conformational sub-states and the conformational populations associated with these sub-states are determined based on one or more of principal component analysis (PCA), normal mode analysis (NMA), time-averaged normal coordinate analysis (TANCA), quasi-harmonic analysis (QHA), and quasi-anharmonic analysis (QAA).

18. One or more non-transitory computer-readable media having computer-executable instructions embodied thereon that, when executed by one or more computing devices, cause the computing devices to perform the following operations:
receive input at a user interface of a computing device, the input selecting a target enzyme;
access biophysical and dynamics data for the target enzyme from a data store, the biophysical and dynamics data comprising data obtained by one or more of NMR, X-ray crystallography, Cryo-EM, neutron scattering, hydrogen-deuterium exchange, and computer simulations;
analyze the biophysical and dynamics data to identify one or more potential allosteric sites located remote from an active site of the target enzyme, the potential allosteric sites being energetically coupled to the active site of the target enzyme through an energy transfer network within the target enzyme;
quantify a level of energetic coupling between each of the one or more potential allosteric sites and the active of the target enzyme;
score each of the potential allosteric sites based on suitability as a druggable site and quantity of energetic transfer from an allosteric site to the active site of the target enzyme;
ranking each of the potential allosteric sites based on highest score;
select a subset of the potential allosteric sites having the highest rank;
computationally screen a plurality of chemical compounds to determine a binding energy between each of the subset of allosteric sites and each of the plurality of chemical compounds;
computationally model a derived set of chemical compounds based on strong binding compounds with different functional groups to improve the binding on the allosteric sites;
computationally model the effect of the chemical compounds binding to each of the plurality of allosteric sites in the derived set;
quantify each of a plurality of conformations of the target enzyme while bound to the chemical compounds and while not bound to the compounds by performing molecular dynamics simulations to model vibrational modes of the enzyme, the plurality of conformations including at least one conformational sub-state associated with increased enzymatic activity of the target enzyme;

rank the chemical compounds based on achieving increased energy flow from an allosteric site to the active site of the target enzyme and increased conformations in the sub-state associated with enzymatic activity;

present a subset of top ranking chemical compounds comprising potential positive allosteric modulators for the target enzyme on the user interface; and validate one or more of the subset of top ranking chemical compounds for use as a positive allosteric modulator for the target molecule using one or more of the following in vitro techniques: spectrophotometric assays, radiometric assays, mass spectrometry, multiple injection method studies, isothermal titration calorimetry studies, stopped-flow kinetics, steady state kinetics, or pre-steady state kinetics measurements.

19. The computer-readable media of claim 18, wherein biophysical and dynamics data is obtained by computational analysis of internal movements of the target enzyme that affect its enzymatic activity.

20. The computer-readable media of claim 18, wherein quantifying a level of energetic coupling comprises performing molecular dynamics simulations to monitor the energy flow between residues within the target enzyme either by creating a temperature gradient or by adding extra kinetic energy at different surface sites of the target enzyme.

* * * * *